(12) United States Patent
Mendelowitz et al.

(10) Patent No.: US 10,842,845 B2
(45) Date of Patent: *Nov. 24, 2020

(54) OXYTOCIN IMPROVES TREATMENT OF OBSTRUCTIVE SLEEP APNEA

(71) Applicant: THE GEORGE WASHINGTON UNIVERSITY, Washington, DC (US)

(72) Inventors: David Mendelowitz, Vienna, VA (US); Vivek Jain, McLean, VA (US); Heather Jameson, Arlington, VA (US); Jay Shawn Kimbro, Stevensville, MD (US)

(73) Assignee: THE GEORGE WASHINGTON UNIVERSITY, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,091

(22) Filed: Nov. 8, 2018

(65) Prior Publication Data
US 2019/0076501 A1 Mar. 14, 2019

Related U.S. Application Data

(63) Continuation of application No. 15/327,252, filed as application No. PCT/US2015/038970 on Jul. 2, 2015, now Pat. No. 10,166,268.

(60) Provisional application No. 62/028,972, filed on Jul. 25, 2014.

(51) Int. Cl.
*A61K 38/095* (2019.01)
*A61K 9/00* (2006.01)

(52) U.S. Cl.
CPC .......... *A61K 38/095* (2019.01); *A61K 9/0043* (2013.01)

(58) Field of Classification Search
None
See application file for complete search history.

(56) References Cited

U.S. PATENT DOCUMENTS

| | | | |
|---|---|---|---|
| 8,753,327 B2 | 6/2014 | Fan | |
| 10,166,268 B2 | 1/2019 | Mendelowitz et al. | |
| 2006/0039867 A1* | 2/2006 | Rao | A61K 31/42 424/45 |
| 2006/0252685 A1* | 11/2006 | Gould | A61K 38/095 514/11.6 |
| 2017/0143790 A1 | 5/2017 | Mendelowitz et al. | |

OTHER PUBLICATIONS

Uvnäs-Moberg et al.,"Maternal plasma levels of oxytocin during physiological childbirth—a systematic review with implications for uterine review with implications for uterine contractions and central actions of oxytocin", BMC Pregnancy and Childbirth,2019, pp. 1-17 (Year: 2019).*

Kurkiewicz et al., "ivery of Aerosolized Medication through Continuous Positive Airway Pressure Device", he Board of Regents of the University of Wisconsin System, 2010 (Year: 2010).*
Armour, J.A., "Potential clinical relevance of the 'little brain' on the mammalian heart." Experimental Physiology (2008); 93:165-176.
Batten, T.F., "Immunolocalization of putative neurotransmitters innervating autonomic regulating neurons (correction of neurones) of cat ventral medulla." Brain Research Bulletin (1995); 37:487-506.
Bazzano et al., "Effect of nocturnal nasal continuous positive airway pressure on blood pressure in obstructive sleep apnea." Hypertension (2007); 50:417-23.
Boychuk et al., "Modulation of bulbospinal rostral ventral lateral medulla neurons by hypoxia/hypercapnia but not medullary respiratory activity." Hypertension (2012); 60:1491-1497.
Bradley et al., "Obstructive sleep apnoea and its cardiovascular consequences." The Lancet (2009); 373:82-93.
Braga et al., "Cardiovascular responses to peripheral chemoreflex activation and comparison of different methods to evaluate baroreflex gain in conscious mice using telemetry." American Journal of Physiology. Regulatory, Integrative and Comparative Physiology (2008); 295:1168-1174.
Braga et al., "Central oxytocin modulates exercise-induced tachycardia." American Journal of Physiology Regulatory Integrative and Comparative Physiology (2000); 278:R1474-82.
Campen et al., "Acute and chronic cardiovascular effects of intermittent hypoxia in C57BL/6J mice." Journal of Applied Physiology (2005); 99:2028-2035.
Carlson et al., Depressed baroreflex sensitivity in patients with obstructive sleep apnea. American Journal of Respiratory and Critical Care Medicine (1996); 154:1490-1496.
Chitravanshi et al., "Microinjection of glycine into the nucleus ambiguus elicits tachycardia in spinal rats." Brain Research (1991); 566:290-294.
Dergacheva et al., "Chronic intermittent hypoxia and hypercapnia inhibit the hypothalamic paraventricular nucleus neurotransmission to parasympathetic cardiac neurons in the brain stem." Hypertension (2014); 64:597-603.
Dergacheva et al., "Developmental changes in GABAergic neurotransmission to presympathetic and cardiac parasympathetic neurons in the brn1nstern." Journal of Neurophysiology (2013); 110: 672-679.
Dyavanapalli et al., "Chronic intermittent hypoxia-hypercapnia blunts heart rate responses and alters neurotransmission to cardiac vagal neurons." Journal of Physiology (2014); 592:2799-811.

(Continued)

*Primary Examiner* — Lianko G Garyu
(74) *Attorney, Agent, or Firm* — Cooley LLP

(57) ABSTRACT

The present disclosure provides methods for treating obstructive sleep apnea (OSA) and OSA induced cardiorespiratory diseases. The disclosure provides, inter alia, methods for treating or alleviating: OSA or OSA induced hypertension, cardiac arrhythmias, myocardial ischemia, sudden cardiac death or stroke, by administering oxytocin. The disclosure further provides methods for improving sleep satisfaction in OSA patients by administering oxytocin.

14 Claims, 16 Drawing Sheets

(56) References Cited

OTHER PUBLICATIONS

Fletcher et al., "Blood pressure response to chronic episodic hypoxia: the renin-angiotensin system." Journal of Applied Physiology (2002); 92:627-633.

Fletcher et al., "Carotid chemoreceptors, systemic blood pressure, and chronic episodic hypoxia mimicking sleep apnea." Journal of Applied Physiology (1992); 72:1978-1984.

Fletcher et al., "Renin activity and blood pressure in response to chronic episodic hypoxia." Hypertension (1999); 34:309-314.

Frank et al., "Mapping and identification of GABAergic neurons in transgenic mice projecting to cardiac vagal neurons in the nucleus ambiguus using photo-uncaging." Journal of Neurophysiology (2009); 101:1755-1760.

Freet et al., "Baroreflex and chemoreflex controls of sympathetic activity following intermittent hypoxia." Autonomic Neuroscience: Basic and Clinical (2013); 174:8-14.

Gamer et al., "Oxytocin specifically enhances valence-dependent parasympathetic responses." Psychoneuroendocrinology (2012); 37:87-93.

Griffioen et al., "Reactive oxygen species mediate central cardiorespiratory network responses to acute intermittent hypoxia." Journal of Neurophysiology (2007); 97:2059-2066.

Gu et al., "Selective impairment of central mediation of baroreflex in anesthetized young adult Fischer 344 rats after chronic intermittent hypoxia." American Journal of Physiology Heart Circulatory Physiology (2007); 293:H2809-2818.

Higa et al., "Baroreflex control of heart rate by oxytocin in the solitary-vagal complex." American Journal of Physiology Regulatory Integrative and Comparative Physiology (2002); 282:R537-45.

Holst et al., "Postnatal oxytocin treatment and postnatal stroking of rats reduce blood pressure in adulthood." Autonomic Neuroscience (2002); 99:85-90.

International Preliminary Report on Patentability for International Application No. PCT/US2015/038970, dated Jan. 31, 2017, 7 pages.

International Search Report for PCT/US2015/038970. Filing date Jul. 2, 2015.

Kannan et al., "Effects of stimulation of the hypothalamic paraventricular nucleus on blood pressure and renal sympathetic nerve activity." Brain Research Bulletin (1988); 20:779-83.

KC et al., "Increased vasopressin transmission from the paraventricular nucleus to the rostral medulla augments cardiorespiratory outflow in chronic intermittent hypoxia-conditioned rats." The Journal of Physiology (2010); 588:725-740.

KC et al., "Modulation of cardiorespiratory function mediated by the paraventricular nucleus." Respiratory Physiology & Neurobiology (2010); 174:55-64.

Kline D.D., "Chronic intermittent hypoxia affects integration of sensory input by neurons in the nucleus tractus solitarii." Respiratory Physiology Neurobiology (2010); 174:29-36.

Kline et al., "Adaptive depression in synaptic transmission in the nucleus of the solitary tract after in vivo chronic intermittent hypoxia: evidence for homeostatic plasticity." Journal of Neuroscience (2007); 27:4663-4673.

Konecny et al., "Obstructive sleep apnea and hypertension: an update." Hypertension (2014); 63:203-209.

Kurkiewicz, et al., "Delivery of Aerosolized Medication through Continuous Positive Airway Pressure Device", The Board of Regents of the University of Wisconsin System (2010); accessed http://bmedesign.engr.wisc.edu/projects/s10/cpap/; pp. 1-31.

Lai et al., "Enhanced sympathetic outflow and decreased baroreflex sensitivity are associated with intermittent hypoxia-induced systemic hypertension in conscious rats." Journal of Applied Physiology (2006); 100:1974-1982.

Lai et al., "Enhanced sympathetic outflow and decreased baroreflex sensitivity are associated with intermittent hypoxia-induced systemic hypertension in conscious rats." Journal of Applied Physiology (1985); 2006;100:1974-82.

Lancel et al., "Intracerebral oxytocin modulates sleep-wake behavior in male rats." Regulatory Peptides (2003); 114(2-3):145-52.

Leung R.S., "Sleep-disordered breathing: autonomic mechanisms and arrhythmias." Progress in Cardiovascular Diseases—Journal (2009); 51:324-38.

Lin et al., "Chronic intermittent hypoxia impairs baroreflex control of heart rate hut enhances heart rate responses to vagal efferent stimulation in anesthetized mice." American Journal of Physiology Heart Circulatory Physiology (2007); 293:H997-1006.

Lin et al., "Structural remodeling of nucleus ambiguus projections to cardiac ganglia following chronic intermittent hypoxia in C57BL/6J mice." Journal of Comparative Neurology (2008); 509:103-117.

Loke et al., "Association of obstructive sleep apnea with risk of serious cardiovascular events: a systematic review and meta-analysis." Circulation Cardiovascular Quality and Outcomes (2012); 5:720-8.

McCall et al., "The animal and human neuroendocrinology of social cognition, motivation and behavior." Nature Neuroscience (2012); 15:681-8.

McCann et al., "Oxytocin, vasopressin and atrial natriuretic peptide control body fluid homeostasis by action on their receptors in brain, cardiovascular system and kidney." Progress in Brain Research (2002); 139:309-28.

Mendelowitz D., "Advances in Parasympathetic Control of Heart Rate and Cardiac Function." News Physiology Science (1999); 14:155-161.

Mendelowitz D., "Firing properties of identified parasympathetic cardiac neurons in nucleus ambiguus." American Journal of Physiology (1996); 271:H2609-2614.

Mendelowitz et al., "Identification and dissociation of cardiovascular neurons from the medulla for patch clamp analysis." Neuroscience Letters, (1991); 132:217-221.

Michelini et al., "Oxytocinergic regulation of cardiovascular function: studies in oxytocin-deficient mice." American journal of physiology. Heart and Circulatory Physiology (2003); 284:H2269-76.

Neff et al., "Prenatal nicotine exposure alters central cardiorespiratory responses to hypoxia in rats: implications for sudden infant death syndrome." Journal of Neuroscience (2004); 24:9261-9268.

Neff et al., "Stimulation of NTS activates NMDA and non-NMDA receptors in rat cardiac vagal neurons in the nucleus ambiguus." Brain Research (1998); 792:277-282.

Parish et al., "Obstructive sleep apnea and cardiovascular disease." Mayo Clinic Proceedings (2004); 79:1036-46.

Peng et al., "Chronic intermittent hypoxia enhances carotid body chemoreceptor response to low oxygen." Advances in Experimental Medicine and Biology (2001); 499:33-38.

Peng et al., "Effect of two paradigms of chronic intermittent hypoxia on carotid body sensory activity." Journal of Applied Physiology (2004); 96:1236-1242; discussion 1196.

Petersson et al., "Oxytocin causes a long-term decrease of blood pressure in female and male rats." Physiology and Behavior (1996); 60:1311-5.

Petersson et al., "Oxytocin decreases blood pressure in male but not in female spontaneously hypertensive rats." Journal of the Autonomic Nervous System (1997); 66:15-8.

Petersson M., "Cardiovascular effects of oxytocin." Progress in Brain Research (2002); 139:281-8.

Pinol et al., "Visualization of oxytocin release that mediates paired pulse facilitation in hypothalamic pathways to brainstem autonomic neurons." PLoS One (2014); 9:e112138.

Ring et al., "Anxiolytic-like activity of oxytocin in male mice: behavioral and autonomic evidence, therapeutic implications." Psychopharmacology (Berl) (2006); 185:218-25.

Sanchez-De-La-Torre et al., "Obstructive sleep apnea and cardiovascular disease." The Lancet Respiratory Medicine (2013); 1:61-72.

Sawchenko et al., "Immunohistochemical identification of neurons in the paraventricular nucleus of the hypothalamus that project to the medulla or to the spinal cord in the rat." The Journal of Comparative Neurology (1982); 205:260-72.

Schuen et al., "The cardiorespiratory response to anoxia: normal development and the effect of nicotine." Respiratory Physiology (1997); 109:231-239.

(56) References Cited

OTHER PUBLICATIONS

Sharpe et al., "Chronic intermittent hypoxia increases sympathetic control of blood pressure: role of neuronal activity in the hypothalamic paraventricular nucleus." American Journal of Physiology Heart Circulatory Physiology (2013); 305:H1772-1780.

Soukhova-O'Hare et al., "Postnatal intermittent hypoxia alters baroreflex function in adult rats." American Journal of Physiology Heart Circulatory Physiology (2006); 290:H1157-1164.

Taylor et al., "Nervous control of heart rate: activity in the cardiac vagus of the dogfish." Journal of Applied Physiology: Respiratory, Environmental and Exercise Physiology (1982); 53:1330-1335.

Trimer et al., "Is there a chronic sleep stage-dependent linear and nonlinear cardiac autonomic impairment in obstructive sleep apnea?" Sleep Breath (2013).

Wang et al., "Characteristics of spontaneous and evoked GABAergic synaptic currents in cardiac vagal neurons in rats." Brain Research (2001); 889:78-83.

Wang et al., "Endogenous acetylcholine and nicotine activation enhances GABAergic and glycinergic inputs to cardiac vagal neurons." Journal of Neurophysiology (2003); 89: 2473-2481.

Willis et al., "Three types of postsynaptic glutamatergic receptors are activated in DMNX neurons upon stimulation of NTS." American Journal of Physiology (1996); 271: RI614-1619.

Written Opinion for PCT/US2015/038970. Filing date of Jul. 2, 2015.

Wsol et al., "Central oxytocin modulation of acute stress-induced cardiovascular responses after myocardial infarction in the rat." Stress (2009); 12:517-25.

Yamashita et al., "Decrease in blood pressure by stimulation of the rat hypothalamic paraventricular nucleus with L-glutamate or weak current." Journal of the Autonomic Nervous System (1987); 19:229-34.

Yan et al., "Attenuation of heart rate control and neural degeneration in nucleus ambiguus following chronic intermittent hypoxia in young adult Fischer 344 rats." Neuroscience (2008); 153:709-720.

Yan et al., "Chronic intermittent hypoxia impairs heart rate responses to AMPA and NMDA and induces loss of glutamate receptor neurons in nucleus ambiguous of F344 rats." American Journal of Physiology Regulatory Integrative and Comparative Physiology (2009): 296:R299-308.

Ye et al., "Patch-clamp studies in the CNS illustrate a simple new method for obtaining viable neurons in rat brain slices: glycerol replacement of NaCl protects CNS neurons." Journal of Neuroscience Methods (2006); 158:251-259.

Young et al., "The occurrence of sleep-disordered breathing among middle-aged adults." New England Journal of Medicine (1993); 328:1230-1235.

Zhao et al., "Cell type-specific channelrhodopsin-2 transgenic mice for optogenetic dissection of neural circuitry function." Nature Methods (2011); 8:745-752.

Zoccal et al., "Chronic intermittent hypoxia augments sympatho-excitatory response to ATP but not to L-glutamate in the RVLM of rats." Autonomic Neuroscience: Basic & Clinical (2011); 165:156-162.

\* cited by examiner

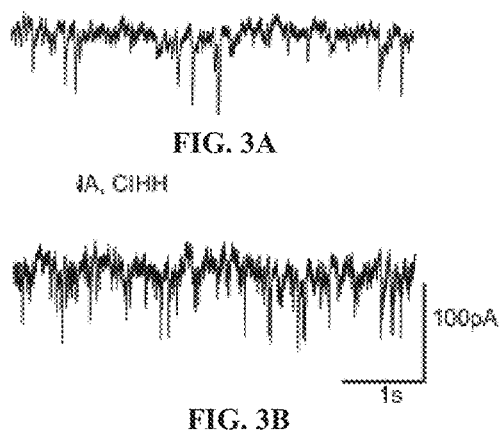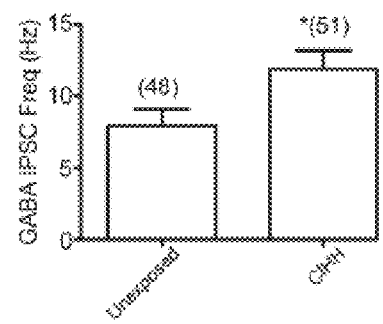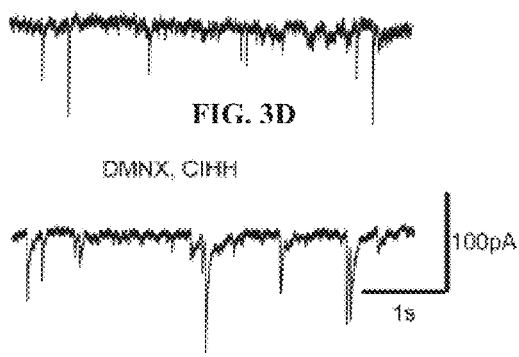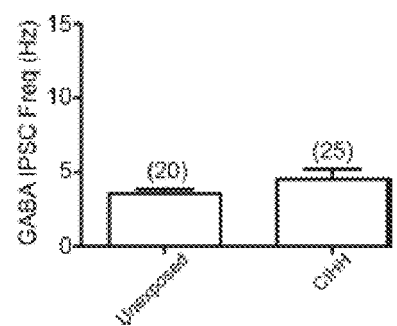
FIG. 3A
FIG. 3B
FIG. 3C
FIG. 3D
FIG. 3E
FIG. 3F Glycine IPSCs

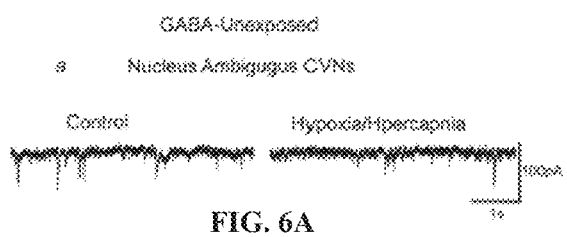
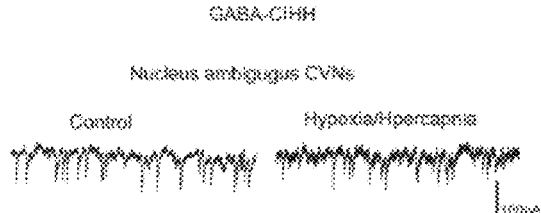
FIG. 6A  FIG. 6G
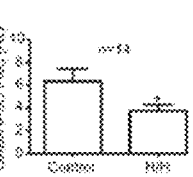 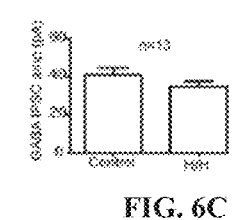  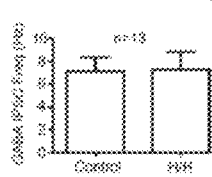 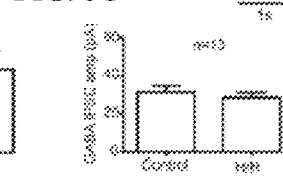
FIG. 6B  FIG. 6C  FIG. 6H  FIG. 6I
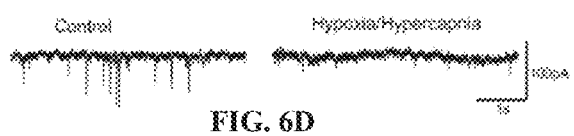
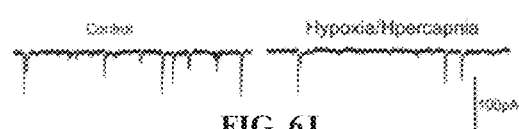
FIG. 6D  FIG. 6J
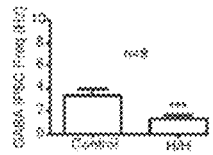 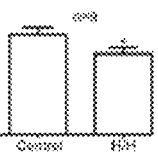  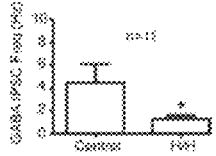 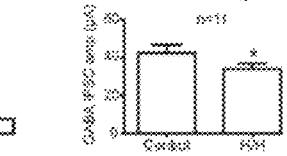
FIG. 6E  FIG. 6F  FIG. 6K  FIG. 6L

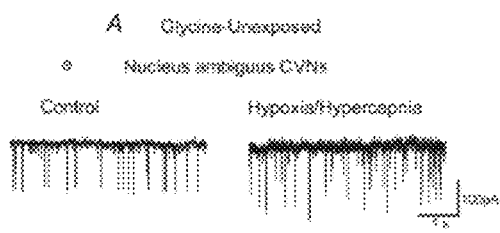
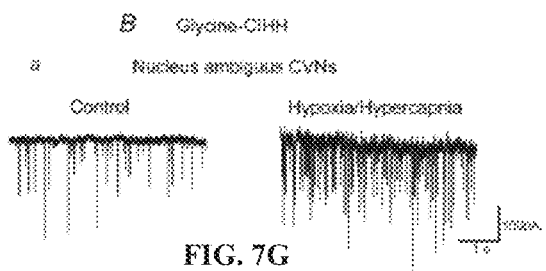
FIG. 7A
FIG. 7G
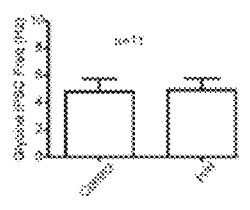
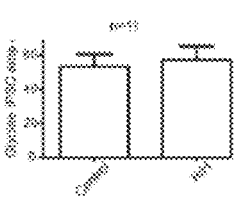
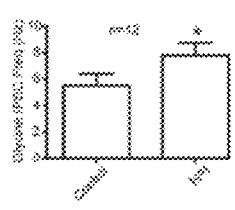
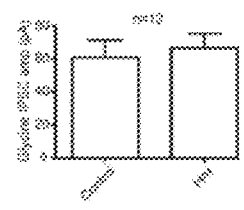
FIG. 7B    FIG. 7C      FIG. 7H    FIG. 7I
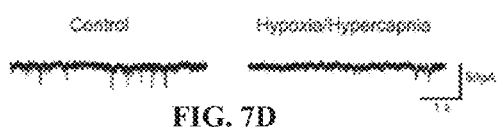
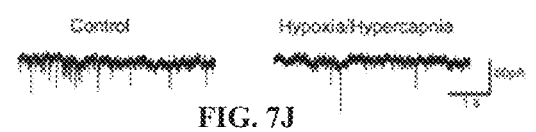
FIG. 7D
FIG. 7J
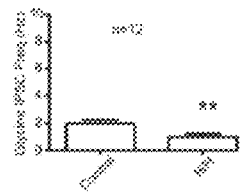
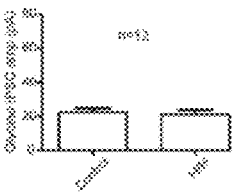
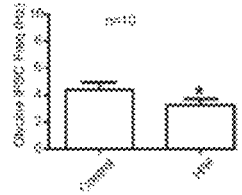
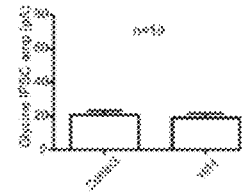
FIG. 7E      FIG. 7F      FIG. 7K      FIG. 7L

OXYTOCIN IMPROVES TREATMENT OF OBSTRUCTIVE SLEEP APNEA

CROSS REFERENCE TO RELATED APPLICATION

The present Application is a continuation of U.S. patent application Ser. No. 15/327,252, filed Jan. 18, 2017, which is a 371 national phase entry of PCT Application No. PCT/US2015/038970, filed Jul. 2, 2015, which claims the benefit of priority to U.S. Provisional Application No. 62/028,972, filed on Jul. 25, 2014, the contents of each of which are hereby incorporated by reference in their entirety.

STATEMENT REGARDING FEDERALLY SPONSORED RESEARCH OR DEVELOPMENT

This disclosure was made with Government support under contract R01-HL72006 awarded by the NIH. The U.S. Government has certain rights in the disclosure.

FIELD OF THE DISCLOSURE

The present disclosure relates to methods and compositions for treating obstructive sleep apnea (OSA) and OSA induced cardiorespiratory diseases. More particularly, the disclosure relates to compositions and methods that are useful for treating OSA and OSA induced hypertension and cardiac dysfunction and to compositions and methods that are useful for improving sleep quality in OSA patients.

BACKGROUND

Patients with obstructive sleep apnea (OSA) experience repetitive collapses of the upper airway during sleep causing intermittent periods of hypoxia and hypercapnia (H/H) accompanied by arterial oxygen desaturations and increases in arterial carbon dioxide levels, ultimately altering both cardiac parasympathetic and sympathetic nervous system activity (Bradley and Floras, 2009; Leung, 2009; Loke et al., 2012). Upon termination of apneas, asphyxia causes a brief arousal from sleep, sympathetic activity increases and vagal tone decreases leading to surges in blood pressure (BP) and heart rate (HR) (Bradley and Floras, 2009; Leung, 2009; Loke et al., 2012). These acute effects of OSA are thought to cause chronic long term changes in cardiovascular dysfunction including hypertension, arrhythmias, and cardiovascular mortality (Bradley and Floras, 2009). Indeed, patients suffering from OSA have increases in blood pressure, lower heart rate variability, and reduced baroreflex sensitivity (Carlson et al., 1996; Trimer et al., 2013; Konecny et al., 2014), with chronic impairment in cardiac autonomic function i.e., sympathetic hyperactivity and diminished parasympathetic activity (Trimer et al. 2013). While identification of the mechanisms underlying the elevations in sympathetic nerve activity in CIH and OSA has been the focus of numerous studies (Fletcher et al., 1999; Fletcher et al., 2002; Kc et al., 2010; Zoccal et al., 2011); studies identifying the characteristics and mechanisms underlying depressed cardiac parasympathetic activity are scarce.

Exposure to chronic intermittent hypoxia (CIH) or hypoxia/hypercapnia (OHM) during the sleeping period of animals mimics the repetitive episodes of HIT that occur in humans with OSA and thus, serve as an animal model of OSA. Similar to what is observed in patients with OSA, animals exposed to CIH or CIH/H experience decreased baroreflex sensitivity, increased sympathetic activity, diminished parasympathetic activity to the heart, and develop hypertension within 3 weeks of CIH/H (Carlson et al, 1996; Dyavanapalli et al., 2014; Lai et al., 1985; Parish and Somers, 2004; Pinol et al., 2014).

The parasympathetic activity to heart arises from cardiac vagal neurons (CVNs) located in the nucleus ambiguous (NA) and dorsal motor nucleus of the vagus (DMNX) that dominate the control of heart rate (Mendelowitz 1999) (FIG. 1). The preganglionic vagal efferent nerve terminals of the CVNs synapse with the postganglionic intracardiac ganglia neurons located within the connective and fat tissue surrounding sinoatrial and atrioventricular nodes (Armour 2008). CVNs are typically intrinsically silent and thus depend on synaptic inputs (glutamatergic, GABAergic, and glycinergic) to dictate their activity (Mendelowitz 1996; Willis et al. 1996; Neff et al. 1998; Wang et al. 2001; Wang et al. 2003).

The paraventricular nucleus of the hypothalamus (PVN) is critical in controlling autonomic function under normal conditions and regulating cardiovascular activity in response to hypoxic stress. The adverse alterations in BP, HR, and respiration that occur with CIH have been postulated to involve pathways from the PVN to sympathetic brainstem nuclei. Recently, it has been hypothesized that different PVN neurons projecting to parasympathetic nuclei, particularly the dorsal vagal complex (DVC) where parasympathetic cardiac control originates, differentially alter autonomic balance (Kc and Dick, 2010). However, much less is known concerning the function and role of the neurotransmission from the PVN to parasympathetic areas of the brainstem in normal and disease states. Consequently, there is a great need in the medical community for understanding the mechanisms underlying the parasympathetic control of cardiac dysfunction and for the development of novel therapeutic compounds, compositions, and methods of treatment, which help alleviate the aforementioned cardiorespiratory side effects associated with OSA.

The present disclosure investigates the mechanisms responsible for diminished parasympathetic control of cardiac functions during OSA and shows that oxytocin-secreting PVN neurons, as well as administration of oxytocin, are novel and powerful targets to mitigate important negative characteristics of the apnea as well as the adverse cardiorespiratory consequences of OSA.

SUMMARY OF THE DISCLOSURE

The present disclosure provides methods of treatment and compositions for treating or alleviating obstructive sleep apnea (OSA) and OSA induced cardiorespiratory diseases and compromised sleep quality.

In aspects, the present disclosure provides methods for treating or alleviating OSA, and OSA induced compromised sleep quality and cardiorespiratory diseases such as hypertension, cardiac arrhythmias, myocardial ischemia, sudden cardiac death, and stroke, said methods comprising, inter alia, administering an effective dose of oxytocin.

In aspects, the disclosure provides that many of the events associated with OSA such as duration of apnea, arousals per hour, increased blood pressure, increased heart rate, oxygen desaturation and compromised sleep quality can be reduced or inhibited by administration of oxytocin.

In some aspects, the present disclosure provides for an improved method of OSA treatment, which comprises administering an effective dose of oxytocin in conjunction with continuous positive airway pressure (CPAP) therapy. In one embodiment, the effective dose of oxytocin may be administered to OSA patients receiving CPAP therapy via the CPAP inhalation system.

In one embodiment, the disclosure provides a method for treating a patient suffering from obstructive sleep apnea, comprising: administering to the patient an effective dose of oxytocin.

In one embodiment, the disclosure provides a method for treating a patient suffering from OSA induced cardiorespiratory disease, comprising: administering to the patient an effective dose of oxytocin. Cardiorespiratory diseases that may be treated or alleviated from the methods of the present disclosure are selected from the group consisting of: hypertension, cardiac arrhythmias, myocardial ischemic, sudden cardiac death, and stroke. In another embodiment, the disclosure provides a method for treating a patient suffering from OSA induced hypertension, comprising: administering to the patient an effective dose of oxytocin.

In some embodiments, the disclosure provides a method for improving sleep quality in a patient suffering from obstructive sleep apnea, comprising: administering to the patient an effective dose of oxytocin.

In one embodiment, the patient suffering from obstructive sleep apnea is receiving CPAP therapy.

In one embodiment, the effective dose of oxytocin is administered intranasally. In one aspect, the effective dose of oxytocin is about 20 International Units (IU) per day. In another aspect, the effective dose of oxytocin is about 30 IU per day. In yet another aspect, the effective dose of oxytocin is about 40 IU per day. In still another aspect, the effective dose of oxytocin is at least 40 IU per day.

In one embodiment, oxytocin is administered closer to the sleeping time of the patient. In another embodiment, oxytocin is administered about 10 minutes, 20 minutes, 30 minutes, 40 minutes, 50 minutes, or about 1 hour prior to sleeping. In yet another embodiment, oxytocin is administered within an hour of the patient falling asleep.

In one aspect, the administration of oxytocin prevents or reduces the risk of developing OSA induced cardiorespiratory diseases in the patient. In another aspect, the administration of oxytocin reduces the hypertension experienced by the patient. In yet another aspect, the administration of oxytocin maintains or decreases the heart rate and/or blood pressure of the patient.

In one aspect, the administration of oxytocin improves sleep quality or sleep satisfaction in the patient. In another aspect, the administration of oxytocin decreases the number of arousals per hour experienced by the patient during sleep. In one aspect, the administration of oxytocin decreases the number of arousals per hour experienced by the patient by at least 10%. In still another aspect, the administration of oxytocin leads to a decrease in the duration of apnea experienced by the patient during sleep. In one aspect, the administration of oxytocin decreases the duration of apnea experienced by the patient by at least 10%. In still another aspect, the administration of oxytocin leads to a decrease in the oxygen desaturation experienced by the patient during sleep.

In some embodiments, the disclosure provides a method for treating a patient suffering from obstructive sleep apnea induced hypertension, comprising: intranasally administering to the patient at least 40 International Units (IU) of oxytocin within an hour of the patient falling asleep.

In one embodiment, the disclosure provides a method for improving sleep quality in a patient suffering from obstructive sleep apnea, comprising: intranasally administering to the patient at least 40 International Units (IU) of oxytocin within an hour of the patient falling asleep, wherein the administration of oxytocin decreases the number of arousals per hour experienced by the subject during sleep. In one aspect, the administration of oxytocin leads to improvement in empirical factors indicative of sleep quality in the patient.

In other embodiments, the disclosure provides a method for treating a patient suffering from obstructive sleep apnea induced hypertension and compromised sleep quality, comprising: intranasally administering to the patient at least 40 International Units (IU) of oxytocin within an hour of the patient falling asleep.

In still other embodiments, the disclosure provides a method for treating obstructive sleep apnea in a patient receiving continuous positive airway pressure (CPAP) therapy, comprising: administering to the patient at least 40 International Units (IU) of oxytocin intranasally via the CPAP inhalation system within an hour of the patient falling asleep.

In one aspect, the disclosure provides a method for treating obstructive sleep apnea in a patient receiving continuous positive airway pressure (CPAP) therapy, comprising: intranasally administering to the patient about 5 International Units (IU) of oxytocin per hour via the CPAP inhalation system for about 8 hours. In another aspect, oxytocin is administered to the patient intranasally via the CPAP inhalation system at the rate of about 5.7 IU/hour for about 7 hours. In yet another aspect, oxytocin is administered to the patient intranasally via the CPAP inhalation system at the rate of about 6.6 IU/hour for about 6 hours. In yet another aspect, oxytocin is administered to the patient intranasally via the CPAP inhalation system at the rate of about 8 IU/hour over the sleep period of 5 hours.

In certain embodiments, the disclosure provides a method for treating a patient suffering from obstructive sleep apnea induced cardiorespiratory disease, comprising: intranasally administering to the patient at least 40 International Units (IU) of oxytocin within an hour of the patient falling asleep.

In some embodiments, the disclosure provides a method for treating a patient suffering from obstructive sleep apnea, comprising: activating oxytocin-secreting neurons in the paraventricular nucleus (PVN) of the hypothalamus.

BRIEF DESCRIPTION OF THE DRAWINGS

FIG. 3A shows representative traces in control conditions showing GABAergic spontaneous IPSCs recorded from CVNs in the NA of unexposed animals while applying glycinergic and glutamatergic blockers. FIG. 3B shows representative traces in control conditions showing GABAergic spontaneous IPSCs recorded from CVNs in the NA of CIH/H exposed animals while applying glycinergic and glutamatergic blockers. FIG. 3C shows the quantitative histograms depicting the frequency of GABAergic IPSCs in CVNs in the NA of unexposed and CIH/H exposed animals. FIG. 3D shows representative traces in control conditions showing GABAergic spontaneous IPSCs recorded from CVNs in the DMNX of unexposed animals while applying glycinergic and glutamatergic blockers. FIG. 3E shows representative traces in control conditions showing GABAergic spontaneous IPSCs recorded from CVNs in the DMNX of CIH/H exposed animals while applying glycinergic and glutamatergic blockers. FIG. 3F shows the quantitative histograms depicting the frequency of GABAergic IPSCs in CVNs in the DMNX of unexposed and CIH/H exposed animals. The numbers in parentheses represent 'n' value. *$p<0.05$, unpaired t-test.

FIG. 6A shows representative traces of GABAergic IPSCs recorded from CVNs in the NA of unexposed animals in control conditions and following H/H exposure for 10 minutes. FIG. 6B shows the histograms depicting the frequency of GABAergic IPSCs recorded from CVNs in the NA of unexposed animals in control conditions and H/H (10 minutes) conditions. FIG. 6C shows the histograms depicting the amplitude of GABAergic IPSCs recorded from CVNs in the NA of unexposed animals in control conditions and H/H (10 minutes) conditions. FIG. 6D shows representative traces of GABAergic IPSCs recorded from CVNs in the DMNX of unexposed animals in control conditions and following H/H exposure for 10 minutes. FIG. 6E shows the histograms depicting the frequency of GABAergic IPSCs recorded from CVNs in the DMNX of unexposed animals in control conditions and H/H (10 minutes) conditions. FIG. 6F shows the histograms depicting the amplitude of GABAergic IPSCs recorded from CVNs in the DMNX of unexposed animals in control conditions and H/H (10 minutes) conditions. FIG. 6G shows representative traces of GABAergic IPSCs recorded from CVNs in the NA of CIH/H exposed animals in control conditions and following H/H exposure for 10 minutes. FIG. 6H shows the histograms depicting the frequency of GABAergic H/H recorded from CVNs in the NA of CIH/H exposed animals in control conditions and H/H (10 minutes' conditions. FIG. 6I shows the histograms depicting the amplitude of GABAergic IPSCs recorded from CVNs in the NA of CIH/H exposed animals in control conditions and H/H (10 minutes) conditions. FIG. 6J shows representative traces of GABAergic IPSCs recorded from CVNs in the DMNX of OHM exposed animals in control conditions and following H/H exposure for 10 minutes. FIG. 6K shows the histograms depicting the frequency of GABAergic IPSCs recorded from CVNs in the DMNX of CIH/H exposed animals in control conditions and H/H (10 minutes) conditions. FIG. 6L shows the histograms depicting the amplitude of GABAergic IPSCs recorded from CVNs in the DMNX of CIH/H exposed animals in control conditions and H/H (10 minutes) conditions.

FIG. 7A shows representative traces of glycinergic IPSCs recorded from CVNs in the NA of unexposed animals in control conditions and following H/H exposure for 10 minutes. FIG. 7B shows the histograms depicting the frequency of glycinergic IPSCs recorded from CVNs in the NA of unexposed animals in control conditions and H/H (10 minutes) conditions. FIG. 7C shows the histograms depicting the amplitude of glycinergic IPSCs recorded from CVNs in the NA of unexposed animals in control conditions and H/H (10 minutes) conditions. FIG. 7D shows representative traces of glycinergic IPSCs recorded from CVNs in the DMNX of unexposed animals in control conditions and following H/H exposure for 10 minutes. FIG. 7E shows the histograms depicting the frequency of glycinergic IPSCs recorded from CVNs in the DMNX of unexposed animals in control conditions and H/H (10 minutes) conditions. FIG. 7F shows the histograms depicting the amplitude of glycinergic IPSCs recorded from CVNs in the DMNX of unexposed animals in control conditions and H/H (10 minutes) conditions. FIG. 7G shows representative traces of glycinergic IPSCs recorded from CVNs in the NA of OHM exposed animals in control conditions and following H/H exposure for 10 minutes. FIG. 7H shows the histograms depicting the frequency of glycinergic IPSCs recorded from CVNs in the NA of CIH/H exposed animals in control conditions and H/H (10 minutes) conditions. FIG. 7I shows the histograms depicting the amplitude of glycinergic IPSCs recorded from CVNs in the NA of CIH/H exposed animals in control conditions and H/H (10 minutes) conditions. FIG. 7J shows representative traces of glycinergic IPSCs recorded from CVNs in the DMNX of CIH/H exposed animals in control conditions and following H/H exposure for 10 minutes, FIG.

7K shows the histograms depicting the frequency of glycinergic IPSCs recorded from CVNs in the DMNX of CIH/H exposed animals in control conditions and H/H (10 minutes) conditions. FIG. 7L shows the histograms depicting the amplitude of glycinergic IPSCs recorded from CVNs in the DMNX of CIH/H exposed animals in control conditions and H/H (10 minutes) conditions.

DETAILED DESCRIPTION

Figure 1:
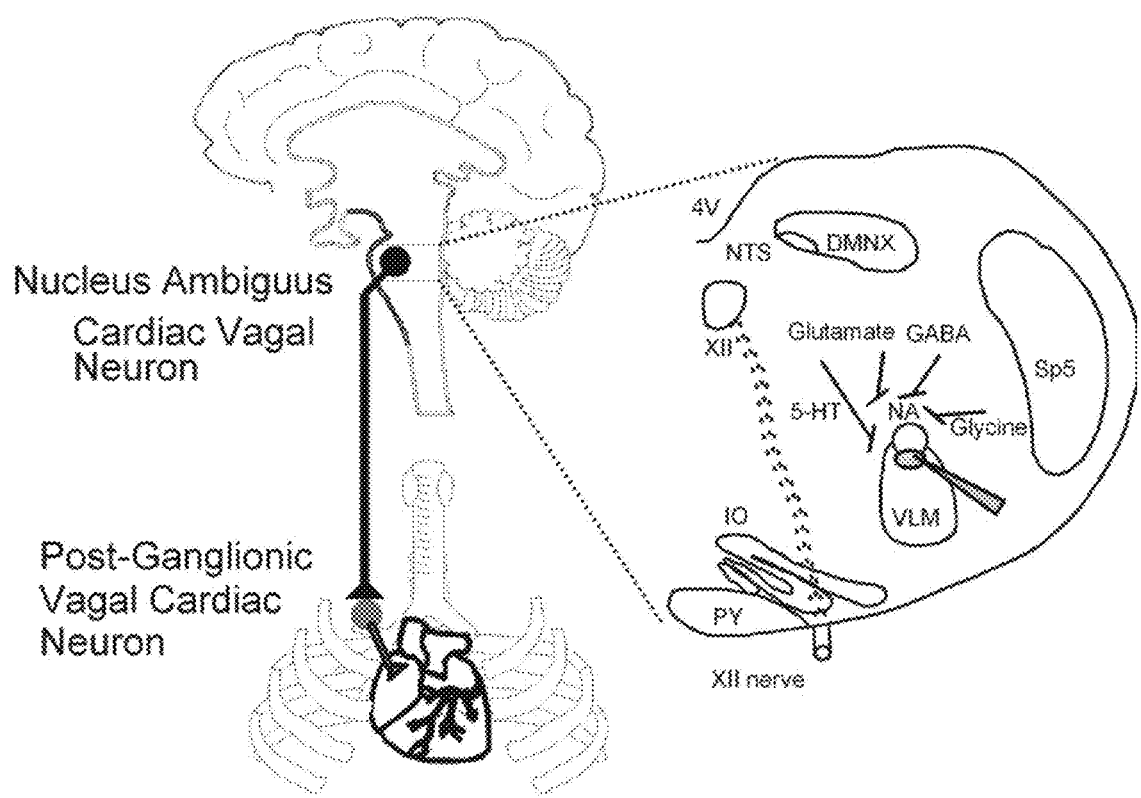
FIG. 1 shows the schematic for parasympathetic control of cardiac function.

Sleep apnea is a common disorder in which an individual have one or more pauses in breathing or shallow breaths while sleeping. The most common type of sleep apnea is obstructive sleep apnea (OSA). In this condition, the upper airway repetitively collapses or becomes blocked during sleep. This causes shallow breathing or breathing pauses. Breathing pauses or the duration of apnea can last from a few seconds to minutes. They may occur 30 times or more an hour. Typically, normal breathing then starts again, sometimes with a loud snort or choking sound.

Breathing pauses in individuals with OSA lead to repetitive intermittent periods of hypoxia/hypercapnia (H/H) during sleep that are accompanied by arterial oxygen desaturations and increases in arterial carbon dioxide levels. OSA is an independent risk factor for the development of hypertension, coronary artery disease, sudden cardiac death and arrhythmias (Sanchez-de-la-Torre et al. 2013). Patients suffering from OSA have increases in blood pressure, lower heart rate variability, and reduced baroreflex sensitivity (Carlson et al. 1996; Trimer et al. 2013; Konecny et al. 2014), with chronic impairment in cardiac autonomic function i.e., sympathetic hyperactivity and diminished parasympathetic activity (Trimer et al. 2013).

Continuous positive airway pressure (CPAP) therapy is the most common treatment for OSA, however this treatment is only modestly effective (Bazzano et al., 2007), not well tolerated by many patients, and its use is often discontinued. Thus, other avenues of treatment are crucial to mitigate the adverse cardiovascular consequences of OSA.

Animal models of OSA based on exposure to chronic intermittent hypoxia (OH) or hypoxia/hypercapnia (OHM) closely mimic OSA in humans (Fletcher et al. 1992; Campen et al. 2005; Kline et al. 2007). While it is known CIH decreases the baroreflex control of heart rate and diminishes parasympathetic activity to the heart, the exact mechanism of how CIH impairs the function of cardiac vagal neurons (CVNs) is not known. The present disclosure elucidates the mechanism of how hypoxia/hypercapnia experienced during OSA leads to cardiac dysfunction and provides methods for treating OSA and OSA-induced cardiac dysfunction by administering an effective dose of oxytocin. The present disclosure is also based, in part, on the surprising discovery that administration of oxytocin to OSA patients also improves sleep quality experienced by these patients.

Methods of Treating/Alleviating Obstructive Sleep Apnea

The present disclosure shows for the first time that administration of oxytocin to OSA patients reduces the duration of apnea experienced by the OSA patients. Accordingly, the present disclosure provides methods for treating OSA in a patient comprising administering to the patient an effective dose of oxytocin.

In one embodiment, oxytocin is administered intranasally; however, other routes of administration such as intravenous, intramuscular, subcutaneous, oral, etc. may also be used. In one embodiment, the effective dose of oxytocin is about 40 International Units (IU) per day. In one aspect, the effective dose of oxytocin is administered closer to the sleeping time of the patient, for instance, about 10 minutes, 20 minutes, 30 minutes, 40 minutes, 50 minutes, or about 60 minutes prior to the patient going to sleep. In another aspect, oxytocin is administered within an hour of the patient falling asleep.

In some embodiments, the OSA patient treated with oxytocin may also be receiving continuous positive airway pressure (CPAP) therapy. CPAP therapy includes wearing an inhalation system that comprises a nasal mask/piece connected via hose to a small machine that supplies air pressure to keep the airways open and prevent airway occlusion.

In certain embodiments, the effective dose of oxytocin is administered to the OSA patient receiving CPAP therapy via the CPAP inhalation system. For instance, in one embodiment, the disclosure provides methods for treating OSA in a patient receiving CPAP therapy, comprising administering to the patient at least 40 IU of oxytocin intranasally via the CPAP inhalation system within an hour of the patient falling asleep. In another embodiment, the disclosure provides methods for treating OSA in a patient receiving CPAP therapy, comprising administering to the patient an effective dose of oxytocin intranasally via the CPAP inhalation system over the duration of the sleep. For example, in one embodiment, the effective dose of oxytocin is 40 IU and it is administered via the CPAP inhalation system at the rate of about 5 IU/hour over the sleep period of 8 hours. In another embodiment, the effective dose of oxytocin is 40 IU and it is administered via the CPAP inhalation system at the rate of about 5.7 IU/hour over the sleep period of 7 hours. In yet another embodiment, the effective dose of oxytocin is 40 IU and it is administered via the CPAP inhalation system at the rate of about 6.6 IU/hour over the sleep period of 6 hours. In yet another embodiment, the effective dose of oxytocin is 40 IU and it is administered via the CPAP inhalation system at the rate of about 8 IU/hour over the sleep period of 5 hours.

In OSA patients, the duration of apnea can vary and may last from a few seconds to minutes. In one embodiment, administration of oxytocin to OSA patients reduces the duration of apnea by at least 10%, 15%, 20%, 25%, 30%, 35%, 40%, 45%, 50%, 55%, 60%, 65%, or 70% compared to the duration prior to the oxytocin treatment.

In one embodiment, administration of oxytocin to the OSA patient reduces or prevents the risk of developing cardiorespiratory diseases in the patient. The cardiorespiratory diseases that may be prevented or alleviated by administration of oxytocin include, but are not limited to hypertension, cardiac arrhythmias, myocardial ischemia, sudden cardiac death and stroke. The present disclosure also shows for the first time that administration of oxytocin to OSA patients improves sleep satisfaction and sleep quality in these patients.

CPAP is the most common treatment for OSA; however, many patients do not comply with CPAP therapy due to problems such as discomfort associated with wearing the nasal mask, difficulty tolerating forced air, dry mouth or nose, etc. In one embodiment, administration of oxytocin in accordance with the present disclosure increases patient compliance with CPAP treatment as oxytocin reduces the duration of sleep apnea and improves sleep quality.

In certain embodiments, the present disclosure provides methods for treating OSA patients that are dissatisfied with their current OSA treatment comprising administering to the patients an effective dose of oxytocin. Administration of oxytocin in accordance with the present disclosure would increase patient compliance with their current OSA treatment. In one embodiment, patients dissatisfied with their current OSA treatment include patients receiving CPAP therapy.

Oxytocin

Oxytocin is a nine amino acid cyclic peptide hormone with two cysteine residues that form a disulfide bridge between positions 1 and 6. Oxytocin is released from the posterior lobe of the pituitary gland and stimulates the contraction of smooth muscle of the uterus during labor and facilitates release of milk from the breast during nursing. Studies have shown that oxytocin, likely released from a different population of PVN neurons, may exert a wide spectrum of other biological effects including control of memory and learning processes, and various types of maternal and sexual behavior. In addition, oxytocin may participate in the control of cardiovascular functions, thermoregulation and fluid balance. Oxytocin is approved by the Food and Drug Administration for intravenous use to induce labor in pregnant women as well as for the treatment of postpartum hemorrhage. At this time, there are no clinical or regulatory guidelines for the use of oxytocin in the treatment of sleep apnea.

The oxytocin peptide for use in the methods described herein can be natural or synthetic, therapeutically or prophylactically active, peptide fragments, peptide analogues, and chemically modified derivatives or salts of active peptides. There are processes described for the production of oxytocin, see for example U.S. Pat. No. 2,938,891 and U.S. Pat. No. 3,076,797; in addition, oxytocin is commercially available. A variety of peptide analogues and derivatives are available and others can be contemplated for use within the present disclosure and can be produced and tested for biological activity according to known methods. Oxytocin analogues may be included, but are not limited to, 4-threonine-1-hydroxy-deaminooxytocin, 4-serine,8-isoleucine-oxytocin, 9-deamidooxytocin, 7-D-proline-oxytocin and its deamino analog, (2,4-diisoleucine)-oxytocin, deamino oxytocin analog, 1-deamino-1-monocarba-E12-Tyr(OMe)]-OT (dCOMOT), carbetocin, 4-threonine, 7-glycine-oxytocin (TG-OT), oxypressin, deamino-6-carba-oxytoxin (dC60), L-371,257 and the related series of compounds containing an ortho-trigluoro-ethoxyphenylacetyl core such as L-374, 943. Oxytocin peptides for use within the present disclosure can be peptides that are obtainable by partial substitution, addition, or deletion of amino acids within a naturally occurring or native peptide sequence. Peptides can be chemically modified, for example, by amidation of the carboxyl terminus (—$NH_2$), the use of D amino acids in the peptide, incorporation of small non-peptidyl moieties, as well as the modification of the amino acids themselves (e.g. alkylation or esterification of side chain R-groups). Such analogues, derivatives and fragments should substantially retain the desired biological activity of the native oxytocin peptide.

Routes and Ranges of Administration of Oxytocin

The route of administration of oxytocin will depend upon the age, weight and/or the physical condition of the patient and timing of administration. In various embodiments, oxytocin can be administered to a patient nasally, orally, intravenously, intradermally, transdermally, subcutaneously, intramuscularly, topically, intrathecally and intracerebroventricularly.

In one embodiment, oxytocin is administered nasally or intranasally. Intranasal delivery has a number of advantageous features including comparatively high bioavailability, rapid kinetics of absorption and avoidance of a first-pass effect in the liver. In regard to patient compliance and ease of use, intranasal administration provides a simple, rapid and non-invasive mode of application. Oxytocin or a pharmaceutical composition comprising oxytocin can be administered to the nasal cavity as a powder, a granule, a solution, a cream, a spray, a gel, a film, an ointment, an infusion, a drop or a sustained-release composition. In one embodiment, oxytocin or a pharmaceutical composition comprising oxytocin can be administered intranasally using the CPAP inhalation system. In these embodiments, oxytocin can be vaporized or aerosolized and provided via the CPAP inhalation system continuously or at regular intervals.

A therapeutically effective dose of oxytocin will depend upon the age, weight and/or the physical condition of the patient and route of administration. In some embodiments, the effective dose of oxytocin may range from about 10-60 IU, 20-50 IU, or 25-45 IU per day. In some embodiments, the effective dose of oxytocin is about 10, 15, 20, 25, 30, 35, 40, 45, 50, 55, or 60 IU per day. In one embodiment, the effective dose of oxytocin is at least 40 IU per day. In another embodiment, the effective dose of oxytocin is at least 40 IU every other day. In yet another embodiment, the effective dose of oxytocin is about 25 or 30 IU per day. In yet another embodiment, the effective dose of oxytocin is at least 25 or 30 IU every other day. In some embodiments, the effective dose of oxytocin is administered weekly. In some embodiments, the therapeutically effective dose of oxytocin is not 10 units administered at the time of sleep or over a 7 hour period. In some embodiments, the therapeutically effective dose of oxytoxin is not administered intramuscularly or intravenously.

The effective dose of oxytocin can be administered in a single dose or in multiple doses, for example, dosages can be administered two, three, four, five, six, seven, eight, nine or ten times daily. In one embodiment, the effective dose of oxytocin is 40 IU and is administered as a one-time nasal spray shortly before sleeping or within an hour of the patient falling asleep.

Preferably, oxytocin is administered closer to the sleeping time or over the duration of sleep. For instance, in one embodiment, the effective dose of oxytocin can be administered about 10, 20, 30, 40, 50 minutes or about an hour prior to sleeping. In another embodiment, the effective dose of oxytocin can be administered within about 10, 20, 30, 40, 50 minutes or about an hour of the patient falling asleep. In some embodiments, the effective dose of oxytocin is administered as a single dose via the CPAP inhalation system within an hour of the patient falling asleep. In some other embodiments, the effective dose of oxytocin is administered via the CPAP inhalation system over the duration of sleep either continuously or at regular intervals.

Treatment of OSA Induced Cardiorespiratory Diseases

OSA represents a major, yet poorly understood cardiovascular risk factor in 24% of males and 9% of females within the US population. Severe OSA increases cardiovascular mortality 4 fold, and even when corrected for other risk factors increases cardiovascular mortality 3 fold. OSA can play a role in both the initiation and progression of several cardiovascular/cardiorespiratory diseases including sudden death, hypertension, arrhythmias, myocardial ischemia and stroke.

Prior studies by the inventors have shown that activation of oxytocin-positive PVN neurons decreases resting heart rate (HR) and blood pressure (BP). However, the activation of oxytocin-positive PVN neurons does not necessarily indicate that oxytocin is the mediator of the observed decrease in HR and BP. These oxytocin neurons secrete many chemicals at their synapse, including fast neurotransmitters. Prior work has shown these oxytocin neurons release the fast neurotransmitter glutamate, and activation of postsynaptic NMDA and AMPA glutamate receptors are primarily responsible for the excitation of cardiac vagal neurons (Pinol et al., 2014). While anatomical work has shown the presence of peptides, including oxytocin, in the projections from the PVN to parasympathetic nuclei, prior work has not demonstrated the release of peptides either in replacement of, or in addition to, fast neurotransmitters (such as glutamate), and electrophysiological studies to date have only demonstrated release of glutamate and activation of fast ligand gated receptors in these pathways (Pinol et al., 2014). The present disclosure shows for the first time that activation of oxytocin-positive PVN neurons evokes endogenous release of oxytocin that is diminished with CIH/H, and that selective activation of oxytocin-secreting PVN neurons during CIH/H exposure both restores oxytocin release and prevents the CIH/H-elicited elevations in BP to hypertensive levels that occurs in untreated animals. That is, the present disclosure shows for the first time that there is release of oxytocin from oxytocin-secreting PVN neurons, and that this release of oxytocin is cardio-protective. The present disclosure also shows that administration of oxytocin in OSA patients decreases the duration of apnea and the arterial oxygen desaturation that occurs during hypoxia/hypercapnia episodes in OSA patients further confirming the cardio-protective role of oxytocin in OSA patients.

In one embodiment, the present disclosure provides a method for treating a patient suffering from OSA induced cardiorespiratory disease, comprising administering to the patient an effective dose of oxytocin. In one embodiment, the effective dose of oxytocin is 40 IU and is administered intranasally within an hour of the patient falling asleep. OSA induced cardiorespiratory diseases that may be treated in accordance with the present disclosure include, but are not limited to, hypertension, cardiac arrhythmias, myocardial ischemia, sudden cardiac death and stroke. The aforementioned method of treating a patient population for cardiorespiratory disease via oxytocin treatment is very surprising given the fact that previous electrophysiological studies have only demonstrated release of glutamate and activation of fast ligand gated receptors in the PVN to parasympathetic nuclei pathways. See, supra, FIG. 1 and Pinol et al., 2014. The inventors have therefore discovered a unique method of treating a heretofore unidentified patient population.

In one aspect, the present disclosure provides a method for treating a patient suffering from OSA induced hypertension, comprising administering to the patient an effective dose of oxytocin. In one embodiment, the effective dose of oxytocin is at least 40 IU and is administered intranasally within an hour of the patient falling asleep.

In another aspect, the present disclosure provides a method for treating a patient suffering from OSA and/or OSA induced hypertension and compromised sleep quality, comprising activating oxytocin-secreting PVN neurons in the patient.

In some embodiments, the patient being treated with oxytocin for OSA induced cardiorespiratory diseases may also be receiving CPAP therapy.

In one embodiment, administration of oxytocin reduces the hypertension experienced by the patient. In another embodiment, administration of oxytocin decreases the heart rate and/or blood pressure of the OSA patient compared to the heart rate and/or blood pressure prior to the treatment with oxytocin. In some embodiments, administration of oxytocin decreases the heart rate and/or blood pressure of the OSA patient by at least 10%, 15%, 20%, 25%, 30%, 35%, 40%, 45%, or 50% compared to the heart rate and/or blood pressure prior to the treatment with oxytocin.

In one embodiment, administration of oxytocin prevents the heart rate and/or blood pressure of the OSA patient from increasing, i.e. oxytocin maintains the heart rate and/or blood pressure to the levels normally found in the patient.

In certain embodiments, administration of oxytocin to a patient suffering from OSA induced cardiorespiratory disease reduces the oxygen desaturation experienced by the patient during apnea episodes. The term "oxygen desaturation" as used herein refers to a decrease in blood oxygen levels from a normal value of 95 percent. In one embodiment, administration of oxytocin reduces the oxygen desaturation experienced by the patient by at least 2%, 3%, 4%, 5%, 6%, 7%, 8%, 9%, 10%, 15%, 20%, 25%, 30%, 35%, 40%, 45%, or 50% compared to the oxygen desaturation prior to the treatment with oxytocin.

Methods of Improving Sleep Quality in OSA Patients

Previous studies have shown that different routes of administration of oxytocin, for example, externally administered oxytocin represented a stressful event and induced arousal and did not promote sleep. For example, Lancet et al. (Regulatory Peptides, 2003, 114: 145-152) showed in rats under basal, stress-free conditions, endogenous oxytocin promotes sleep whereas acute icy infusion of oxytocin delayed sleep onset latency, which resulted in a transient reduction of non-REMS and REMS, and augmented high-frequency activity in the electroencephalogram (EEG) within non-REMS. Lancet et al. concluded that external icy administration of oxytocin reflected a condition of stress and was accompanied by behavioral arousal and increase vigilance.

Sleep apnea is a stressful event as it represents a strong adverse challenge to the cardiorespiratory system that impedes the breathing process necessary to supply oxygen to the rest of the body. The present disclosure, however, unexpectedly found that, in contrast to previous studies, external administration of oxytocin to OSA patients improved sleep quality or sleep satisfaction in these patients. Accordingly, in one embodiment, the present disclosure provides methods for improving sleep quality in a patient suffering from OSA, comprising administering to the patient an effective dose of oxytocin. In one embodiment, the effective dose of oxytocin is at least 40 IU and is administered intranasally within an hour of the patient falling asleep. The aforementioned method of improving sleep quality is counterintuitive in view of references such as the above cited Lancet, et al. and represents a significant advancement in sleep medicine.

In one embodiment, administration of oxytocin to OSA patients decreases the number of arousals per hour experienced by the patient leading to better sleep. "Arousals" are defined as "abrupt changes in EEG frequency, which last for >3 seconds, and are preceded by at least 10 seconds of EEG sleep." Frequency of arousals is denoted by "arousal index" (arousals/hour) and correlates positively with feelings of non-refreshing sleep, i.e. higher the arousal index, more likely the patient will complain of non-refreshing sleep. In some embodiments, administration of oxytocin to OSA patients decreases the number of arousals per hour experienced by the patient by at least 10%, 15%, 20%, 25%, 30%, 35%, 40%, 45%, or 50% compared to the number of arousals per hour prior to the treatment with oxytocin.

In some embodiments, the quality of sleep or sleep satisfaction in OSA patients is assessed by asking the patients to rank their responses on the scale of 1-5 to a set of empirical factors. For instance, in one embodiment, a set of empirical factors includes the following parameters or questions:

I feel more refreshed than usual this morning
My quality of sleep last night was better than usual
I slept deeper than usual last night
I woke up fewer times than usual last night
I slept longer than usual last night
I feel better overall than usual this morning The patients are asked to rank their response to the above empirical factors on the scale of 1-5 as follows:
1—Strongly disagree
2—Slightly disagree
3—Neither agree nor disagree
4—Slightly agree
5—Strongly agree Based on their responses, a sleep score for each patient is calculated. In one embodiment, administration of oxytocin to OSA patients leads to improvement in empirical factors or sleep score indicative of sleep quality in the OSA patient.

In one embodiment, administration of oxytocin to OSA patients decreases the duration of apnea experienced by the patients leading to better sleep. In one embodiment, administration of oxytocin to OSA patients reduces the duration of apnea by at least 10%, 15%, 20%, 25%, 30%, 35%, 40%, 45%, 50%, 55%, 60%, 65%, or 70% compared to the duration prior to the oxytocin treatment.

Pharmaceutical Compositions

While it is possible to administer oxytocin alone, there may be situations wherein it is advantageous to present it as part of a pharmaceutical composition. Thus, in some aspects of the present invention, oxytocin is administered as a pharmaceutical composition. The pharmaceutical composition can comprise oxytocin at a therapeutically effective dose together with one or more pharmaceutically acceptable carriers and optionally other ingredients. A suitable carrier is one which does not cause an intolerable side effect, but which allows oxytocin to retain its pharmacological activity in the body. A carrier may also reduce any undesirable side effects of oxytocin. A suitable carrier should be stable, i.e., incapable of reacting with other ingredients in the formulation. A suitable carrier should have minimal odor or fragrance or a positive (pleasant) odor. A suitable carrier should not irritate the mucosa, epithelium, underlying nerves or provide a health risk. It may be an accepted transcutaneous or percutaneous carrier or vehicle, because any carrier that can effectively penetrate the stratum corneum of the skin should be highly efficacious in not only penetrating mucosa, but also allowing rapid absorption of substances into the submucosal tissues, nerve sheaths and nerves.

Suitable nontoxic pharmaceutically acceptable carriers will be apparent to those skilled in the art of pharmaceutical formulations. Also see Remington: The Science and Practice of Pharmacy, 20th Edition, Lippincott, Williams & Wilkins (2000). Typical pharmaceutically acceptable carriers include, but are not limited to, mannitol, urea, dextrans, lactose, potato and maize starches, magnesium stearate, talc, vegetable oils, polyalkylene glycols, ethyl cellulose, poly (vinylpyrrolidone), calcium carbonate, chitosan, ethyl oleate, isopropyl myristate, benzyl benzoate, sodium carbonate, gelatin, potassium carbonate, silicic acid, and other conventionally employed acceptable carriers. Other carriers include, but are not limited to, phosphatidylcholine, phosphatidylserine, and sphingomyelins.

The choice of a suitable carrier will depend on the exact nature of the particular formulation desired, e.g., whether the drug is to be formulated into a liquid solution (e.g., for use as drops, for use in an injection, as a spray or impregnated in a nasal tampon, or other agent-impregnated solid), a suspension, a ointment, a film or a gel. If desired, sustained-release compositions, e.g. sustained-release gels, films, transdermal patches, etc. can be readily prepared. The particular formulation will also depend on the route of administration. In one embodiment, a composition comprising oxytocin can be administered to the nasal cavity as a powder, a granule, a solution, a cream, a spray, a gel, a film, an ointment, an infusion, a drop or a sustained-release composition.

To enhance delivery into or across the nasal mucosal surface and/or absorption of a pharmaceutical composition comprising oxytocin, an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery) of the composition. Absorption enhancing compounds may include, but are not limited to, surfactants, bile salts, dihydrofusidates, bioadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

This disclosure is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the disclosure.

EXAMPLES

Example 1

Labeling of CVNs:

To obtain electrophysiological recordings from CVNs, neonatal Sprague-Dawley rats (postnatal days 2-5, Hilltop Laboratory animals Inc, Scottdale, Pa., USA) were anesthetized using hypothermia by cooling to approximately 4° C. A right thoracotomy was performed and retrograde tracer X-Rhoda-mine-5-(and-6)-isothiocyanate (Invitrogen, USA) was then injected into the fat pads at the base of the heart to retrogradely label CVNs (Mendelowitz & Kunze 1991). The animals were then allowed to recover until they were 3-4 weeks old.

Telemetry Implantation:

To record blood pressure and heart rate, male Sprague-Dawley rats, 3-4 weeks of age, were anesthetized using isoflurane (2-4%) and a HD-XII pressure transmitter was implanted (Data Sciences International, St Paul, Minn., USA) with its cathether inserted into the abdominal aorta to record pressure and EKG leads were attached subcutaneously to obtain EKG recordings and heart rate. All rats with telemetry devices were allowed 7-14 days to recover from transmitter implantation surgery before any measurements were recorded. Blood pressure and heart rate were recorded via radio-frequency signals obtained through the Ponemah data acquisition system (Data Sciences International). Baseline recordings of blood pressure and heart rate were obtained for 3 days prior to CIH/H exposure. Prior to, and during, the 28 day CIH/H exposure period daily baseline recordings of blood pressure and heart rate were recorded.

Air or CHI/H Exposure:

Animals were exposed to repetitive cycles of 3 minutes of mild H/H (6% $O_2$+5% $CO_2$+89%, $N_2$) followed by 3 minutes of normoxia (21% $O_2$+79% $N_2$), repeated for 10 times per hour, 8 hr/day, for 3 or 4 weeks. The animals were exposed to CIH/H for 8 hours during light phase and to normal air during the remaining 16 hr. Unexposed animals that were exposed to normal air (21% $O_2$+79% $N_2$), were placed adjacent to the chambers during the exposure period to undergo similar handling, general lab conditions, and background noise as the CIH/H group.

In Vitro Brainstem Slice Preparation:

The methodology described by Ye and colleagues (Ye et al. 2006) was used to obtain viable brainstem slices from mature animals. According to this method, glycerol base artificial cerebrospinal fluid (aCSF) was used for cardiac perfusion and brainstem slicing. Glycerol-based aCSF contained (in mM): 252 glycerol, 1.6 KCl, 1.2 $NaH_2PO_4$, 1.2 MgCl, 2.4 $CaCl_2$, 26 $NaHCO_3$, and 11 glucose. Immediately following air or CIH/H exposure for 4 weeks, rats were anaesthetized using isoflurane and placed on ice. Glycerol aCSF (4° C., pH: 7.4, bubbled with 95% $O_2$-5% $CO_2$) was perfused transcardially at a speed of ~10 ml/min after which the brain was quickly removed, glued on to a stage using 2% low melt agarose and placed in a vibrotome containing glycerol aCSF. Brainstem slices (330 µm thickness) containing either DMNX or NA or brainstem slices containing dorsal motor nucleus (DMV) and channelrhodopsin (ChR2)-containing PVN fibers were obtained and briefly placed in a solution with following composition (in mM): 110 N-methyl-d-glucamine (NMDG), 2.5 KCl, 1.2 $NaH_2PO_4$, 25 $NaHCO_3$, 25 glucose, 110 HCl, 0.5 $CaCl_2$, and 10 $MgSO_4$ equilibrated with 95% $O_2$ and 5% $CO_2$ (pH 7.4) at 34° C. for 1 5 min. NMDG based aCSF was used to help slices recover and to maintain viable brainstem slices for electrophysiological recordings (Zhao et al. 2011). The slices were then mounted in a recording chamber constantly perfused with a normal aCSF with following composition (in mM): 125 NaCl, 3 KCl, 2 $CaCl_2$, 26 $NaHCO_3$, 5 glucose and 5 HEPES; oxygenated with 95% $O_2$-5% $CO_2$ (pH-7.4) and allowed to recover for at least 30 minutes before an experiment was performed.

Electrophysiological Recordings:

CVNs in NA and DMNX were identified by the presence of fluorescent tracer rhodamine and imaged using differential interference contrast optics and infrared illumination. Whole cell voltage clamp recordings from CVNs were done using Axopatch 200B and pClamp 8 software (Axon Instruments, Union city, USA), at a holding voltage of −80 mV at room temperature. The patch pipettes (2.5-5 MΩ) were filled with a solution consisting (in mM) of KCl (150), $MgCl_2$ (4), EGTA (10), Na-ATP (2) and HEPES (10) or K-gluconic acid (150), HEPES (10), EGTA (10), $MgCl_2$ (1) and $CaCl_2$ (1) at a pH of 7.3 for recording inhibitory or excitatory events respectively. For PVN studies, forebrain slices were used for electrophysiology recordings.

Drugs were focally applied to CVNs using a pneumatic picopunp pressure delivery system. GABAergic inhibitory post synaptic currents (IPSCs) were isolated by focal application of solution containing strychnine (1 µM, glycine receptor antagonist), 6-cyano-7-nitroquinoxaline-2, 3-dione (CNQX, 50 µM, non-NMDA receptor antagonist) and D-2-amino-5-phosphonovalerate (APS, 50 µM, NMDA receptor antagonist), with the puffer pipette positioned near the patched neuron. Glycinergic IPSCs were isolated by including gabazine (25 µM, GABA-A receptor antagonist), CNQX, and APS in the puffer pipette. The puffer pipette was filled with gabazine and strychnine to isolate glutamatergic excitatory postsynaptic currents (EPSCs).

Acute H/H:

The respective EPSCs or IPSCs were recorded in control conditions for 5 min in the presence of aCSF equilibrated with 95% $O_2$+5% $CO_2$. Brainstem slices containing CVNs were exposed to H/H by superfusing the aCSF equilibrated with 85% $N_2$+6% O2+9% $CO_2$ for 10 min, Gabazine, strychnine, or CNQX, and APS were applied at the end of each experiment to confirm the targeted isolation of GABAergic, glycinergic, or glutamatergic activity, respectively. Each slice was exposed to hypoxia only once limiting the experiments to only one CVN per slice of tissue. Gabazine, strychnine, CNQX, and APS were obtained from Sigma Aldrich (St. Louis, Mo., USA).

Viral Vectors, Plasmids, and Promoter Constructs:

Lentiviral plasmids pLenti-Syn-hChR2(H134R)-EYFP-WPRE, packaging plasmid pCMV-ΔR8.74 and envelope plasmid pMD2.G were all kindly donated by K. Deisseroth (Stanford University, Stanford, Calif., USA). The pLenti-Syn-hChR2(H134R)-EYFP-WPRE viral vector was produced according to customary protocols as described before (Wsol et al., 2009).

A rat minimal oxytocin (OXT) promoter element from ~530 bp to +33 relative to the origin of transcription of the OXT gene (UCSC genome browser on rat November 2004 assembly; chr3:118,193,690 to 118,194,252) was synthesized de novo and flanked by multiple cloning sites (Genscript, Piscataway, N.J.) (McCann et al., 2002; Petersson et al., 1996). The rAAV1-OXT-Cre was produced using the OXT promoter fragment in the following way (MIT, Viral Gene Transfer Core): pFB-AAV-OXT promoter Cre was created by cloning the OXT promoter into V032 by excising the OXT promoter/pUC57 with XbaI (5') and AgeI (3') and cloning it into V032 cut with SpeI (5') and AgeI (3'). Then Cre was added by cutting Cre out of pBS185 with XhoI (5') and MluI-blunt (3') and moving it into pFB-AAV-OXT cut with XhoI (5') and Asp718-blunt (3'). To achieve robust and highly selective expression of designer receptors exclusively activated by designer drugs (DREADDs) in PVN OXT neurons, the reporter viral vector AAV2-hSyn-DIO-hM$_3$D (G$_q$)-mCherry (UNC, Gene Therapy Center, Vector Core Services) was co-injected with AAV-OXT-Cre. Expression of these Cre-dependent vectors will only be initiated in neurons selectively expressing Cre as they contain silencing double-foxed inverse open reading frames (Sawchenko and Swanson, 1982). OXT receptors, as well as the red fluorescent calcium indicator, were expressed in Chinese hamster ovary (CHO) cells as previously described (Gainer and Buchel, 2012).

Stereotactic Injections:

Stereotactic injections were performed as previously described (Bradley and Floras, 2009; Parish and Somers, 2004; Pinol et al. 2014), pLenti-Syn-hChR2(H134R)-EYFP-WPRE (90-100 nl) was injected for experiments involving activation of channelrhodopsin (ChR2)-expressing PVN fibers, while 20-30 nl of viral vectors rAAV1-OXT-Cre and AAV2-hSyn-DIO-hM$_3$D(G$_q$-mCherry at a 1:2 ratio was injected for PVN OXT neuron activation.

Calcium Imaging in OXT Receptor-Expressing CHO Cells:

Visualization of CHO cells expressing OXT receptors and the calcium indicator, as well as ChR2-containing PVN fibers, were performed on a confocal microscope system as previously described (Gamer and Buchel, 2012). To examine activation of OXT receptors upon optogenetic activation of ChR2-expressing PVN fibers in the DMV, CHO cells were pipetted onto the dorsal motor nucleus (DMV) of brain stem slices from animals previously injected with pLenti-Syn-hChR2(H134R)-EYFP-WPRE into the PVN, OXT-sensitive CHO cells within the boundaries of the DMV and in close apposition to ChR2-containing PVN fibers (7.5±0.5 μm) were used for experiments.

Daily Activation of DREADDs:

1-2 weeks after telemetry implantation, DREADDs receptors on PVN OXT neurons were activated daily by intraperitoneal (IP) injection of clozapine-n-oxide (CNO, 1.0 mg/kg). To investigate the effects of CNO on resting BP and HR in both DREADDs-expressing and sham animals, 3 days prior to CIH/H exposure (control days) baseline BP and HR values were recorded for a 20 min period before CNO injection. Animals from each group then received an IP injection of CNO, BP and HR were recorded for 1 hr, and the animals then underwent exposure to air for 8 hr to achieve acclimation to the chambers. During the 21 days of CIH/H exposure, baseline recordings of BP and HR were obtained before CNO injection, recorded for 1 hr post CNO injection, and for the entire duration of OHM exposure.

Data Analysis for Studies Directed to the Effects of CIH/H on CVNs:

Synaptosoft software (version 6.0.3; Synaptosoft, Decatur, Ga.) was used to analyze the synaptic events recorded from CVNs. Threshold value was set to the root mean square of noise levels multiplied by 5. The frequency and amplitudes of synaptic currents were grouped in 10 sec bins and averaged for 2 min at the end of control and H/H The data were presented as mean±SEM. To examine the chronic changes in blood pressure and heart rate over the 28 day CIH/H exposure, daily values recorded before each CIH/H exposure were statistically analyzed by One-way repeated-measures analysis of variance (One-way ANOVA) followed by Bonferroni's multiple comparison test. Students unpaired t-test was used to compare statistical significance between unexposed and CIH/H exposed groups. For acute H/H evoked blood pressure and heart rate responses during CIH/H exposure and in-vitro experiments utilizing different conditions in the same CVN, Student's paired t-test was used to test the significance using Graphpad Prism 5 software (La Jolla, Calif., USA). Data with $p<0.05$ was considered significant; in the figures, * denotes $p<0.05$,  denotes $p<0.01$, * denotes $p<0.001$.

Data Analysis for Studies Directed to the Effects of CIH/H on PVNs:

Calcium responses in CHO cells were grouped into 0.5 sec bins for a total of 10 bins with the $3^{rd}$ bin (time 0) representing the time of ChR2-expressing PVN fiber activation. Results are presented as percent control and statistically compared with data from the same experiment using a one-way ANOVA with repeated-measures followed by Bonferroni's multiple comparison test. For those experiments comparing CHO cell responses in unexposed brainstem tissue to exposure, a one-way ANOVA was used. Data with $p<0.05$ was considered significant.

Changes in the action potential firing frequency were determined using the MiniAnalysis version 6.0.3 software (Synaptosoft, Decatur, Ga.) and grouped into 5 min bins for a total of 12 bins with the $2^{nd}$ bin representing the start of CNO application. Results are presented as means±SE and statistically compared with control data from the same experiment using a one-way ANOVA with repeated-measures followed by Bonferroni's multiple comparison test for all experiments. Data with $p<0.05$ were considered significant.

To examine the effects of CNO on and the chronic changes to mean arterial blood pressure (MAP) over the 21 days of OHM exposure, values were recorded before and after CNO injection on control days prior to CIH exposures, and days 1, 3, 6, 9, 12, 15, 18, and 21 of CIH/H. Changes within the DREADDs-expressing animals and the sham animals were statistically analyzed by one-way ANOVA with repeated-measures followed by Bonferroni's multiple comparison test. To examine the statistical changes in MAP between the two groups of animals, a two-way ANOVA with repeated-measures followed by Bonferroni's multiple comparison test was used. Data with p<0.05 were considered significant.

Software used for all statistical analysis of the data included Graphpad Prism 4.01 (Graphpad Software, San Diego, Calif.), MicroCal Origin 7.0 (OriginLabs Corp, Nothhampton, Mass.) and Microsoft Excel (Microsoft Corp., Redmond, Wash.).

Example 2

Effect of CIH/H on Blood Pressure

Figure 2A:
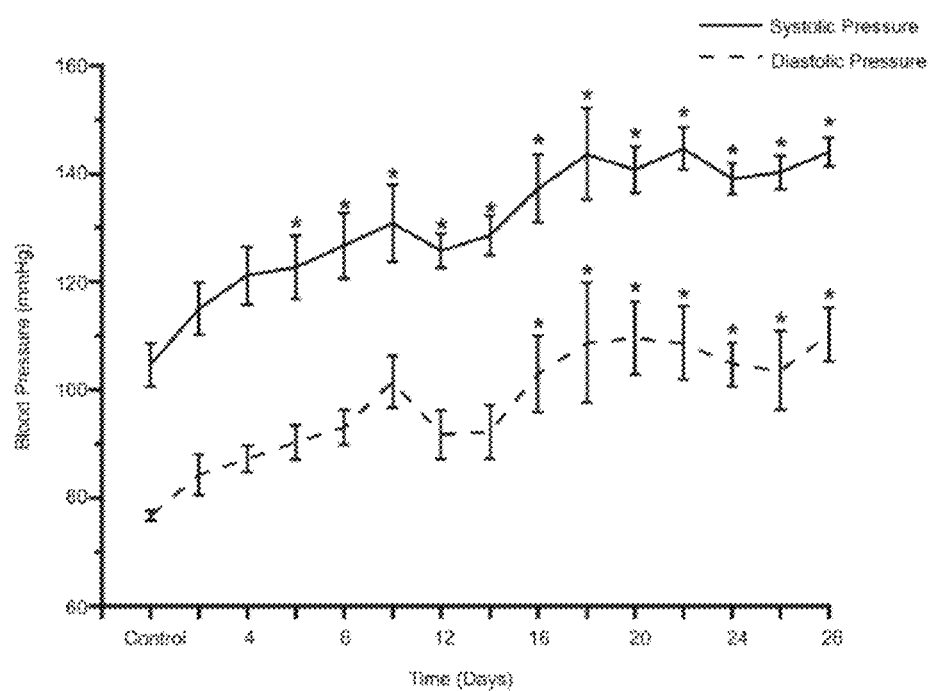
FIG. 2A shows changes in systolic and diastolic blood pressure from day 1 (control) to day 28 of CIH/H exposure. Systolic (solid line) and diastolic (dash line) blood pressures significantly increased from day 6 and day 16, respectively, compared to day 1 control and reached to hypertensive levels by day 21. n=6; *p<0.05; One way ANOVA. The values represent an average blood pressure value recorded for 20 minutes during exposure to air in days prior to and during CIH/H exposures.

Adult rats (4 weeks old) were exposed to CHI/H for 8 hours and to normal air during the remaining 16 hours for 3 weeks as explained above. Blood pressure and heart rate was examined before and throughout 28 days of ORE exposure. After 4 weeks of CIH/H, systolic and diastolic pressure increased to hypertensive levels (from a systolic pressure of 105±4.0 mmHg at the onset of CIH/H to 144±3.0 mmHg after 28 days of CIH/H, n=6; p<0.05; One way ANOVA, and diastolic pressure increased from 77±1.0 mmHg to 110±5.0 mmHg after 28 days of CIH/H, n=6; p<0.05; One way ANOVA), see FIG. 2A.

Example 3

Figure 2B:
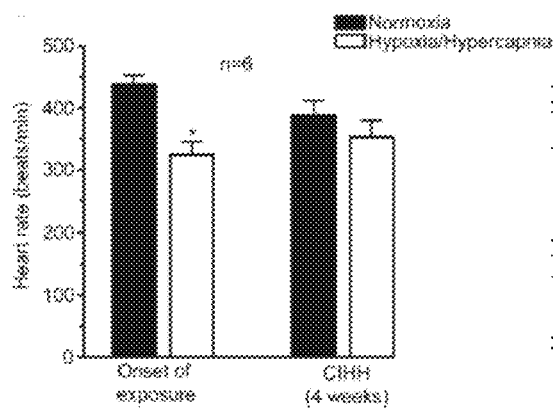
FIG. 2B shows changes in heart rate in response to normoxia and an acute bout of H/H (3 mins) at the onset and after 4 weeks of CIH/H exposure. n=6; *p<0.05; Student's paired t-test.
Figure 2C:
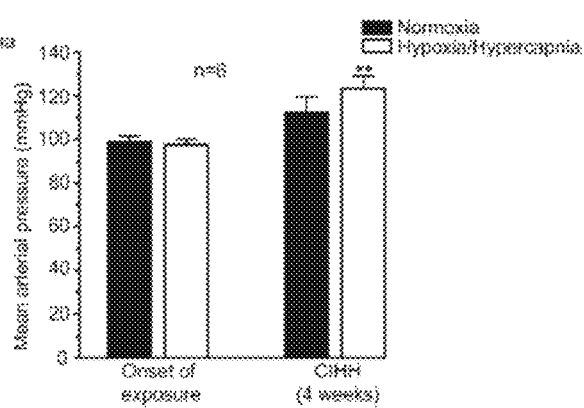
FIG. 2C shows changes in mean arterial blood pressure (MAP) in response to normoxia and an acute bout of H/H (3 mins) at the onset and after 4 weeks of CIH/H exposure. n=6; **p<0.05; Student's paired t-test.
Figure 4A:
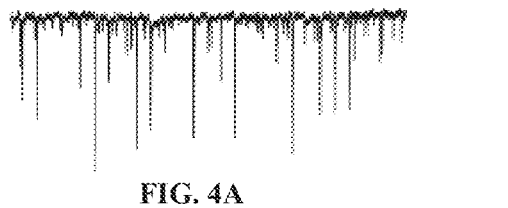
FIG. 4A shows representative traces in control conditions showing glycinergic IPSCs recorded from CVNs in the NA of unexposed animals while applying GABAergic and glutamatergic blockers.
Figure 4B:
FIG. 4B shows representative traces in control conditions showing glycinergic IPSCs recorded from CVNs in the NA of CIH/H exposed animals while applying GABAergic and glutamatergic blockers.
Figure 4C:
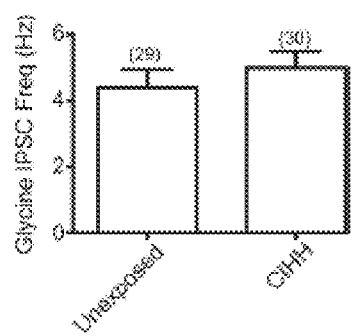
FIG. 4C shows the quantitative histograms depicting the frequency of glycinergic IPSCs in CVNs in the NA of unexposed and CIH/H exposed animals.
Figure 4D:
FIG. 4D shows representative traces in control conditions showing glycinergic. IPSCs recorded from CVNs in the DMNX of unexposed animals while applying GABAergic and glutamatergic blockers.
Figure 4E:
FIG. 4E shows representative traces in control conditions showing glycinergic IPSCs recorded from CVNs in the DMNX of CIH/H exposed animals while applying GABAergic and glutamatergic blockers.
Figure 4F:
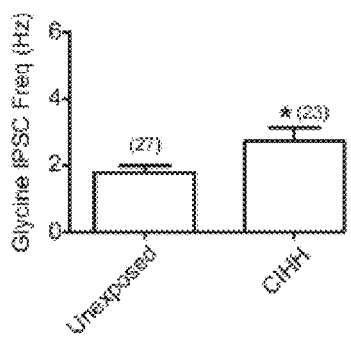
FIG. 4F shows the quantitative histograms depicting the frequency of glycinergic IPSCs in CVNs in the DMNX of unexposed and CIH/H exposed animals. The numbers in parentheses represent 'n' value. *$p<0.05$, unpaired t-test.

Acute H/H Evoked Blood Pressure and Heart Rate Responses at the Start and End of CIH/H Exposure At the beginning of the 28 days of CIH/H exposures, during a single exposure to heart rate decreased by 25% (438±15 beats/min in normoxia and 325±21 beats/min in acute H/H; n=6; p<0.05; paired t-test), and this decrease in heart rate occurred without significant changes in blood pressure (99±2 mmHg in normoxia and 97±3 mmHg in acute H/H; n=6; p>0.05; paired t-test). However, at the end of 4 weeks of CIH/H exposure, acute H/H evoked a significant increase in blood pressure (112±7 mmHg in normoxia and 123±5 mmHg in acute H/H; n=6; p<0.01; paired t-test) while there were no significant changes in heart rate (389±23 beats/min in normoxia and 353±27 beats/min in acute H/H; n=6; p>0.05; paired t-test), see FIGS. 2B and 2C.

Example 4

Actions of CHI/H on Inhibitory Neurotransmission to CVNs

GABAergic and glycinergic IPSCs were examined from CVNs both in the NA and DMNX of the brainstem from unexposed and CIH/H animals. In unexposed animals, the frequency of both GABAergic (7.9±1.2 Hz, n=48 in NA and 3.5±0.3 Hz, n=20 in DMNX; p<0.05; Unpaired t-test) and glycinergic (4.4±0.6 Hz, n=29 in NA and 1.8±0.2 Hz, n=27 in DMNX; p<0.001; Unpaired t-test) IPSCs in NA CVNs was greater than that in DMNX CVNs, see FIGS. 3C, 3F, 4C, and 4F. In addition, the amplitude of glycinergic IPSCs in CVNs of DMNX was significantly less than that of NA (58.6±9.8 pA, n=29 in NA and 23.6±1.5 pA, n=27 in DMNX; p<0.01; Unpaired t-test). The amplitudes of GABAergic IPSCs in NA and DMNX CVNs were not different (44.0±2.5 pA, n=48 in NA CVNs and 46.6±4.3 pA, n=20 in DMNX CVNs; p>0.05).

CIH/H exaggerated the frequency of GABAergic (but not glycinergic) IPSCs in NA CVNs, whereas glycinergic (but not GABAergic) IPSC frequency was increased in DMNX CVNs following OHM. The frequency of GABAergic IPSCs recorded from NA CVNs of CIH/H exposed animals was 49% greater than that in unexposed animals (7.9±1.2 Hz, n=48 in unexposed and 11.8±1.3 Hz, n=51 in CIH/H exposed; p<0.05; unpaired t-test), FIGS. 3A-3C. In DMNX, no change in GABAergic IPSC frequency to CVNs was observed between unexposed and exposed animal groups (3.5±0.3 Hz, n=20 in unexposed and 4.5±0.7 Hz, n=25 in OHM exposed; p>0.05; unpaired t-test), FIGS. 3D-3F. The amplitude of GABAergic IPSCs to CVNs of NA and DMNX in unexposed group was not different from that of CIH/H exposed group.

With respect to glycinergic IPSCs to CVNs, their frequency and amplitudes in CIH/H and unexposed groups were not different in NA CVNs. However, in DMNX CVNs, the frequency of glycinergic IPSCs from CIH/H group was 50% greater compared to unexposed group (1.8±0.2 Hz, n=27 in unexposed and 2.7±0.4 Hz, n=23 in CIH/H exposed; p<0.05; unpaired t-test); see FIGS. 4A-4F.

Example 5

Actions of CIH/H on Excitatory Glutamatergic Neurotransmission to CVNs

Figure 5A:
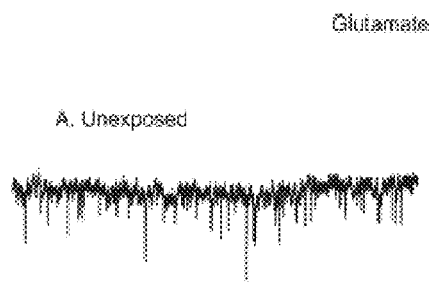
FIG. 5A shows representative traces in control conditions showing glutamatergic EPSCs recorded from CVNs in the NA of unexposed animals while applying GABAergic and glycinergic blockers.
Figure 5C:
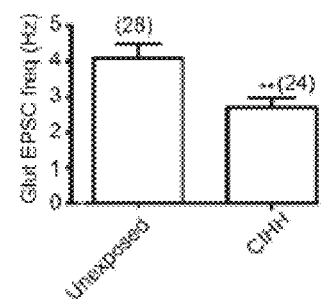
FIG. 5C shows the bar graph depicting the frequency of glutamatergic EPSCs in CVNs in the NA of unexposed and CIH/H exposed animals.
Figure 5B:
FIG. 5B shows representative traces in control conditions showing glutamatergic EPSCs recorded from CVNs in the NA of CIH/H exposed animals while applying GABAergic and glycinergic blockers.
Figure 5D:
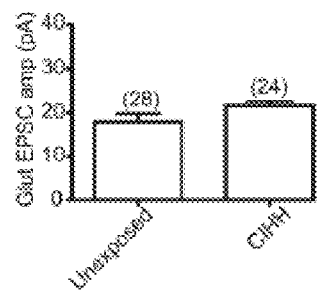
FIG. 5D shows the bar graph depicting the amplitude of glutamatergic EPSCs in CVNs in the NA of unexposed and CIH/H exposed animals.
Figure 5E:
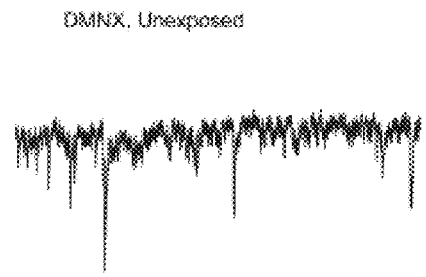
FIG. 5E shows representative traces in control conditions showing glutamatergic EPSCs recorded from CVNs in the DMNX of unexposed animals while applying GABAergic and glycinergic blockers.
Figure 5G:
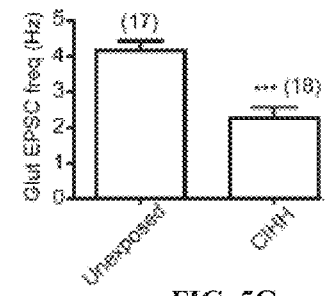
FIG. 5G shows the bar graph depicting the frequency of glutamatergic EPSCs in CVNs in the DMNX of unexposed and OHM exposed animals.
Figure 5F:
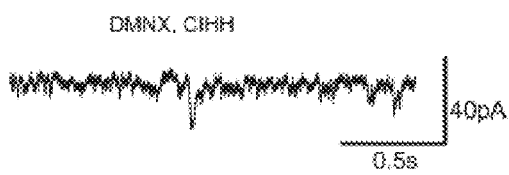
FIG. 5F shows representative traces in control conditions showing glutamatergic. EPSCs recorded from CVNs in the DMNX of CIH/H exposed animals while applying GABAergic and glycinergic blockers.
Figure 5H:
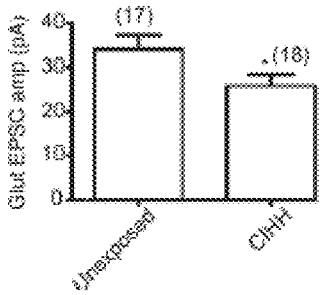
FIG. 5H shows the bar graph depicting the amplitude of glutamatergic EPSCs in the DMNX of unexposed and CIH/H exposed animals. The numbers in parentheses represent 'n' value. *$p<0.05$, unpaired t-test.

The amplitude of EPSCs in NA CVNs was significantly less than the amplitude of EPSCs in DMNX CVNs (18.0±1.8 pA, n=28 in NA and 34.1±1.9 pA, n=19 in DMNX; p<0.001; Unpaired t-test). CIH/H significantly reduced the frequency of glutamatergic EPSCs in CVNs in both NA (4.0±0.4 Hz, n=28 in unexposed and 2.7±0.3 Hz, n=24 in OHM exposed; p<0.01; unpaired t-test) and DMNX (4.1±0.3 Hz, n=17 in unexposed and 2.3±0.3 Hz, n=18 in CIH/H exposed; p<0.001; unpaired t-test) compared to unexposed group, see FIGS. 5C and 5G—. CIH/H also reduced the amplitude of EPSCs in DMNX, but not NA, CVNs (34.1±3.2 pA, n=17 in unexposed and 25.8±2.5 pA, n=18 in CIH/H exposed; p<0.05; unpaired t-test), FIGS. 5D and 5H.

Example 6

Effect of Acute H/H on Inhibitory Neurotransmission to CVNs in Unexposed Animals GABA: In unexposed animals acute exposure to H/H inhibited the frequency of GABAergic IPSCs by 40% and 60% in the NA and DMNX CVNs respectively (NA CVNs: 6.3±1.0 Hz in control and 3.7±0.5 Hz in H/H; n=14; p<0.05; paired t-test, DMNX CVNs: 3.4±0.5 Hz in control and 1.3±0.3 Hz in H/H; n=9; p<0.001; paired t-test), see FIGS. 6B and 6E. In addition, H/H inhibited the amplitude of GABAergic IPSCs in DMNX CVNs (52.5±3.7 pA in control and 42.4±3.5 pA in H/H; n=9; p<0.05; paired t-test) but not in CVNs within the NA, see FIGS. 6C and 6F.

Glycine: Acute H/H inhibited the frequency of glycinergic IPSCs in DMNX CVNs by 50% (2.0±0.3 Hz in control and 1.0±0.2 Hz in H/H; n=12; p<0.01; paired t-test). However the frequency and amplitude of glycinergic IPSCs in NA CVNs were unaltered by acute H/H, see FIGS. 7A-7F.

Example 7

Effect of Acute H/H on Inhibitory Neurotransmission to CVNs in Exposed Animals GABA: Similar to the responses in the unexposed group, in animals exposed to CIH/H acute H/H inhibited the frequency of GABA IPSCs in DMNX CVNs by 60% (4.5±1.6 Hz in control and 1.3±0.3 Hz in H/H; n=11; p<0.05; paired t-test), see FIG. 6K. In contrast, in CIH/H animals the GABAergic responses to acute K/H on NA CVNs was abolished (7.1±1.2 Hz in control and 7.2±1.5 Hz in H/H; n=13; >0.05; paired t-test), see FIGS. 6G-6I.

Similar to the responses in the unexposed animal group, in animals exposed to OHM acute RE reduced the amplitude of GABA IPSCs in DMNX CVNs (42.3±4.5 pA in control and 33.8±3.1 pA in H/H; n=11; p<0.05; paired t-test) but not in NA CVNs, see FIGS. 6I and 6L.

Glycine: Unlike the unexposed animals, in animals exposed to CIH/H acute H/H significantly increased the frequency of glycinergic IPSCs in NA CVNs by 40%, without any significant changes in glycinergic IPSC amplitude (5.5±0.9 Hz in control and 7.8±0.9 Hz in H/H; n=12; p<0.05; paired t-test), see FIGS. 7H and 7I. In animals exposed to CIH/H, acute H/H inhibited the frequency of glycinergic IPSCs in DMNX CVNs by 25%; see FIG. 7K.

Example 8

Effect of Acute H/H on Glutamatergic Neurotransmission to CVNs of Unexposed and CIH/H Exposed Animals Acute H/H had no effect on the frequency or amplitude of glutamatergic EPSCs to CVNs in NA and DMNX in both unexposed and CIH/H exposed animals (Data not shown).

Example 9

Figure 8A:
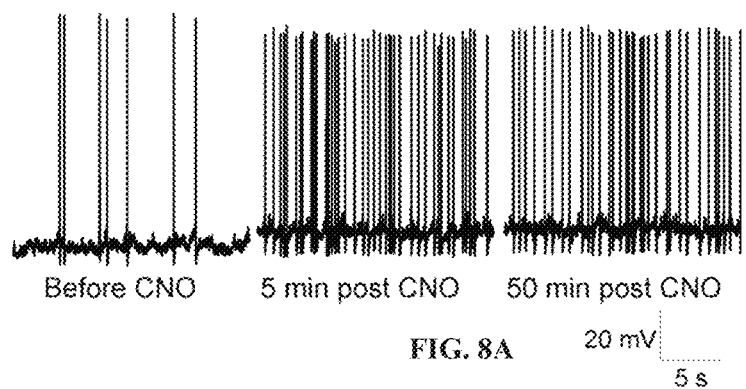
FIG. 8A shows representative action potential firing recorded in current-clamp configuration from a PVN OXT neuron expressing DREADDs before CNO and post CNO indicating excitatory DREADDs activation with CNO application significantly increases the firing of PVN OXT neurons.
Figure 8B:
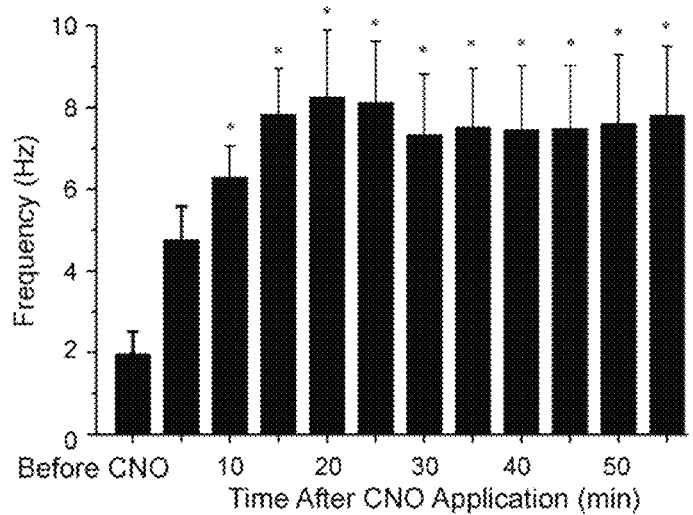
FIG. 8B shows quantitative bar charts depict the frequency of action potentials before and after CNO application in 7 PVN OXT neurons expressing DREADDs. *$p<0.0001$; one-way ANOVA.

Selectivity and In Vitro Activation of Excitatory DREADDs in PVN OXT Neurons Selective excitatory DREADDs expression in PVN OXT neurons was achieved with injection into the PVN of two viral vectors, one expressing Cre under an OXT promoter (rAAV1-OXT-Cre), and the other a Cre-dependent vector expressing excitatory hM$_3$D(G$_q$) DREADDs (AAV2-hSyn-DIO-hM$_3$D(G$_q$)-mCherry). Immunohistochemical analysis confirmed that this viral expression system elicited high (83.1±2.1%) selectivity for DREADDs expression in PVN OXT neurons. The responses upon activation of DREADDs in PVN OXT neurons was assessed in vitro using the whole-cell patch clamp method. The action potential firing frequency of DREADDs-expressing PVN neurons significantly increased within 5 min of CNO application (from 0.19±0.05 Hz to 0.75±0.14 Hz; n=7; *p<0.01; one-way ANOVA; FIGS. 8A-8B). These experiments indicate that CNO application significantly increases the firing of DREADDs-expressing PVN neurons.

Example 10

The Effects of on OXT Receptor Activation

Figure 9A:
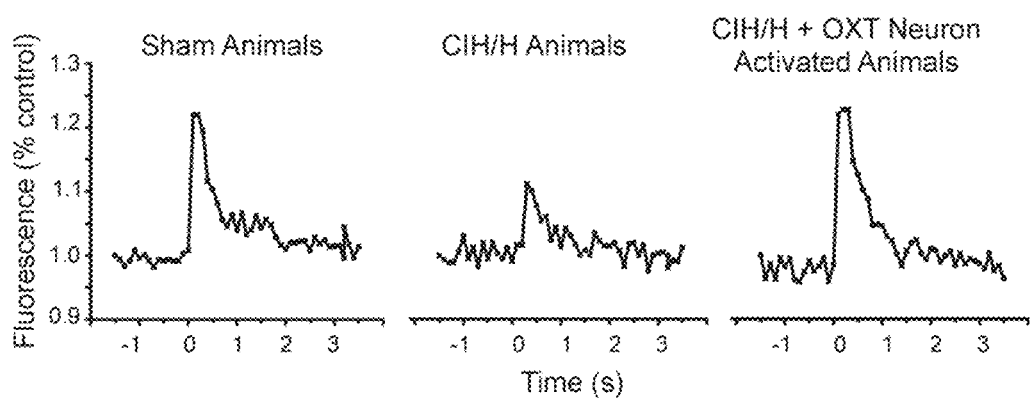
FIG. 9A shows representative responses from CHO cells due to the release of oxytocin, as measured by activating oxytocin receptors and subsequent increase in intracellular calcium levels, deposited onto brainstem tissue taken from animals chronically exposed to air, CIH/H, and CIH/H with daily PVN OXT neuron activation.
Figure 9B:
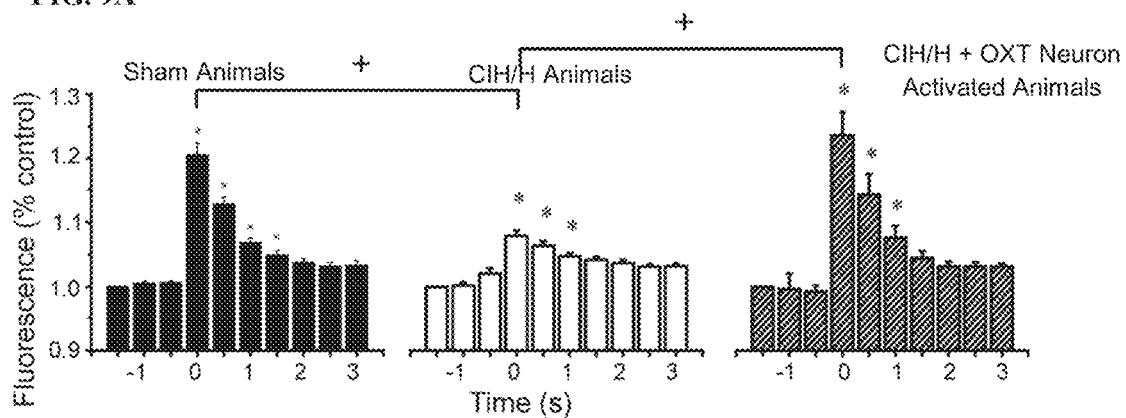
FIG. 9B shows quantitative bar charts depicting the percent control fluorescence of CHO cell responses, as measured by an increase in intracellular calcium levels, in brainstem tissue taken from animals exposed to air (n=14), CIH/H (n=16), and CIH/H with daily OXT neuron activation n=17). *$p<0.05$; one-way ANOVA with repeated measure. $^+p<0.05$; one-way ANOVA.

In order to examine if the release of OXT from PVN fibers is altered with CIH/H, the responses in OXT-sensitive CHO cells were examined in brainstem tissue from unexposed sham and CIH/H exposed animals. Photoactivation of ChR2-containing PVN fibers in the DMV of brainstem slices from unexposed animals evoked large, reproducible, and transient increases in intracellular calcium levels in OXT-sensitive CHO cells (average increases of 21.1±0.02% from baseline during first second; n=14; *p<0.05; one-way ANOVA with repeated measures; FIG. 9B, "sham animals"). CHO cell responses upon PVN fiber stimulation in brainstem slices from animals exposed to CIH/H was significantly depressed (average increases of 8.1±0.01% from baseline during first second; n=16; *p<0.05; one-way ANOVA with repeated measures; FIG. 9B, "CIH/H animals") compared to responses in unexposed animals (+p<0.05; one-way ANOVA; FIG. 9B, "CIH/H animals"). These results indicate the release of OXT from PVN fibers in the DMV is significantly decreased following CIH/H exposure. To examine if restoration of OXT neuron function during CIH/H could restore responses in OXT-sensitive CHO cells, PVN OXT neurons were activated daily before and during CIH/H by daily injections of CNO to activate PVN OXT neurons via excitation of DREADDs receptors in PVN OXT neurons. In animals with chronic activation of OXT neurons the responses in OXT-sensitive CHO cells upon photostimulation of ChR2-containing PVN fibers in the DMV were restored and not significantly different from responses in air exposed control animals (average increases of 23.4±0.03% from baseline during first second; n=17; *p<0.05; one-way ANOVA with repeated measures; FIG. 9B, "CH/H OXT neuron activated animals"). These restored responses in DREADDs-expressing animals were however, significantly increased compared to CIH/H exposed animals (+p<0.05; one way ANOVA; FIG. 9B, "CIH/H OXT neuron activated animals"). These data indicate that OXT released from PVN fibers in the DMV is diminished with CIH/H, but that this release can be restored with chronic PVN OXT neuron activation.

Example 11

Figure 10A:
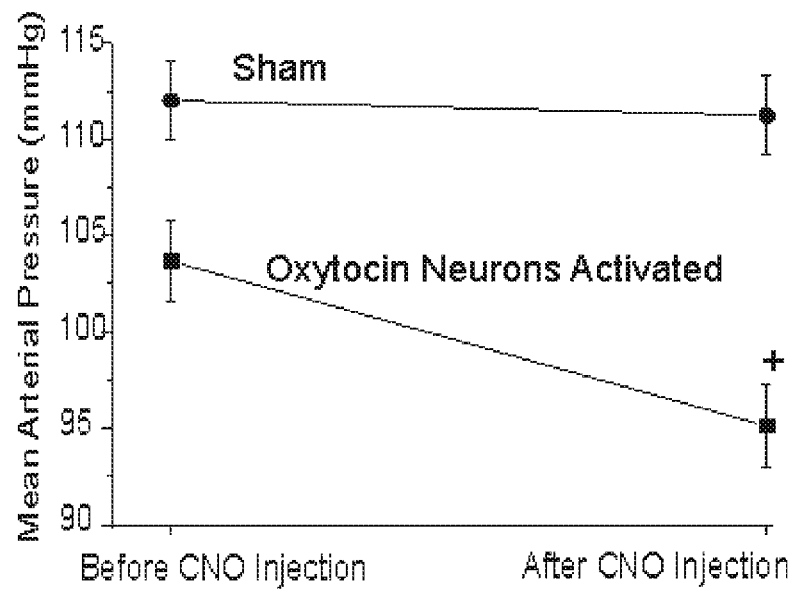
FIG. 10A shows changes in resting MAP before and after CNO injection to activate PVN oxytocin neurons. MAP in oxytocin neuron activated animals was significantly decreased 45 min after CNO injection (n=8; $^+p<0.0001$, one-way ANOVA). In sham animals, CNO injection did not significantly change MAP (n=7; one-way ANOVA).
Figure 10B:
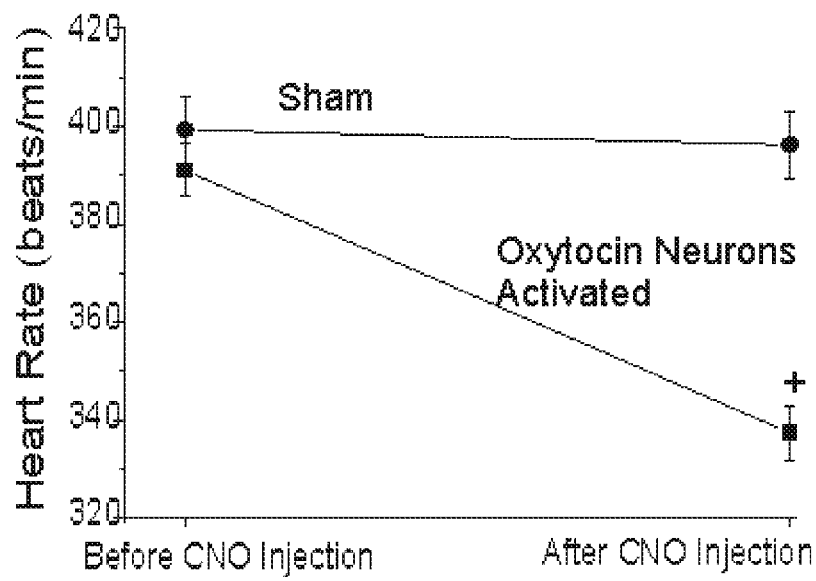
FIG. 10B shows changes in the heart rate (HR) in response to CNO injection. 45 min after CNO injection, HR in DREADDs-expressing was significantly decreased (n=8; $^+p<0.0001$, one-way ANOVA), while CNO injection did not significantly change HR in sham animals (n=7; one-way ANOVA). The values for both MAP (FIG. 10A) and HR (FIG. 10B) represent the averages of each recorded 20 min prior to CNO injection and 45 min after CNO injection on control days.

Acute PVN OXT Neuron Activation Decreases Resting Blood Pressure and Heart Rate CNO administration had no effect on BP represented as mean arterial pressure (MAP) and HR in sham animals without DREADDs expression (FIGS. 10A and 10B). However, CNO administration that activates DREADDs receptors in PVN OXT neurons decreased resting HR and BP throughout 21 days of CIH/H exposure, with significant decreases in MAP (104±2.6 mmHg before CNO to 93±1.7 mmHg after CNO; n=8; +p<0.0001; paired t test; FIG. 10A) and HR (416±7.1 beats/min before CNO to 362±10.5 beats/min after CNO; n=8; +p<0.01; paired t test; FIG. 10B). These data indicate that selective activation of PVN OXT neurons decreases resting BP and HR in conscious unrestrained telemetry instrumented animals.

Example 12

Figure 11:
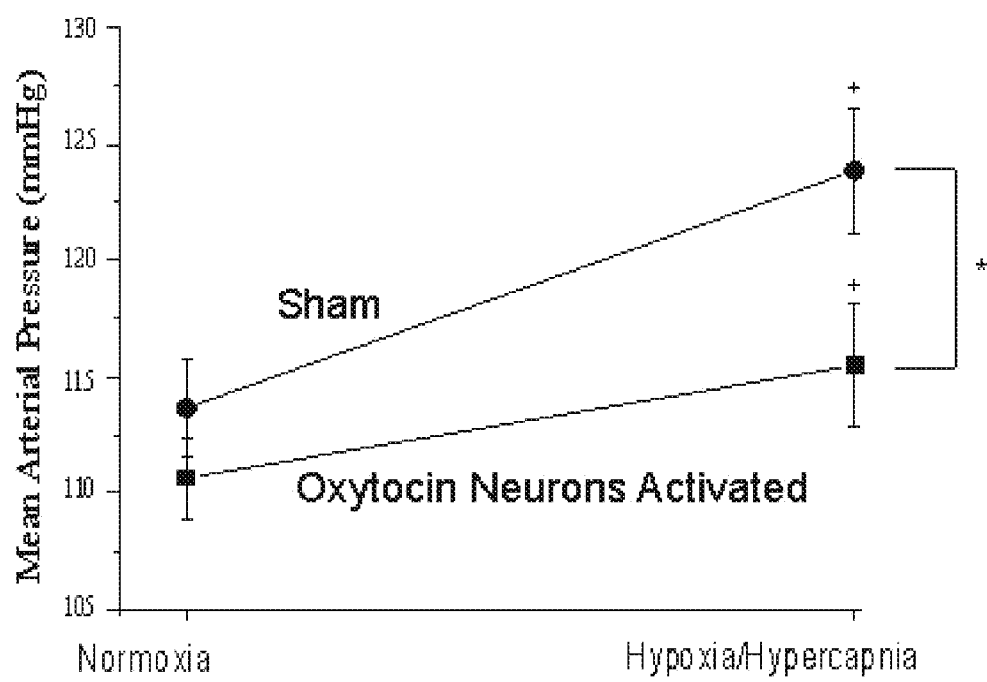
FIG. 11 shows that the activation of oxytocin neurons blunts the increase in blood pressure that occurs with hypoxia/hypercapnia.

Activation of Oxytocin Neurons Blunts the Increase in BP that Occur with to Hypoxia/Hypercapnia Activation of oxytocin neurons also blunted the increase in blood pressure that occurred with hypoxia/hypercapnia (FIG. 11). Activation of oxytocin neurons was achieved by selective expression and subsequent activation of the excitatory Designer Receptors Exclusively Activated by Designer Drugs (DREADDs) virally expressed in paraventricular hypothalamus oxytocin neurons upon microinjection of both an adeno-associated (AAV) floxed DREADDS virus and a lentivirus virus that selectively drives CRE expression under the control of the oxytocin promoter.

Example 13

Figure 12:
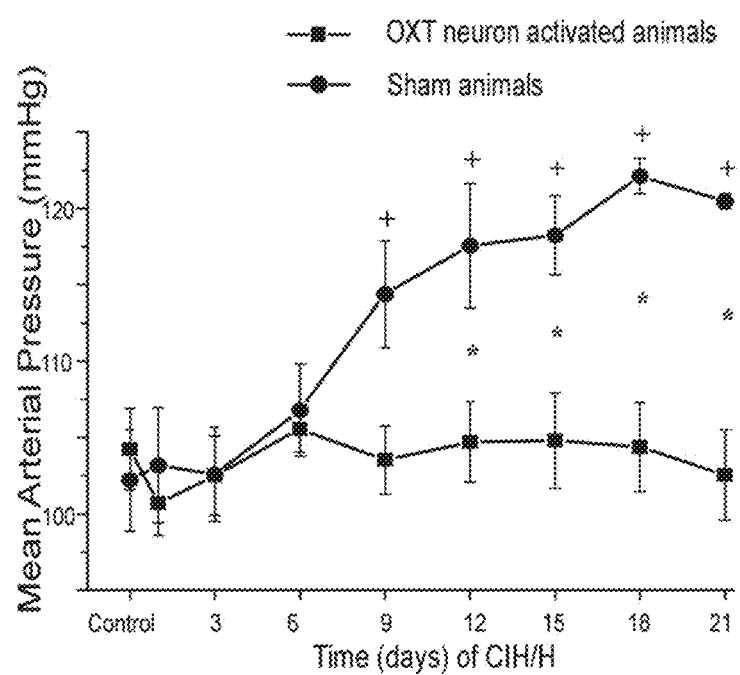
FIG. 12 shows changes in MAP from control days to day 21 of CIH/H exposure. MAP in sham animals significantly increased from day 9 to day 21 compared to control day and reached hypertensive levels by day 12 (n=7; $^+p<0.0001$, one-way ANOVA). MAP did not significantly increase in DREADDs-expressing OXT neuron activated animals over the 21 days of CIH/H exposure compared to control days (n=8; one-way ANOVA). MAP significantly increased in sham animals compared to DREADDs-expressing animals from day 12 to day 21 (*$p<0.0001$, two-way ANOVA with repeated measures).

Chronic PVN OXT Neuron Activation Prevents the Development of Hypertension that Occurs with CIH/H To test if activation of PVN OXT neurons alters the changes in BP that occur with CIH/H, MAP was examined before and throughout 21 days of CIH/H exposure in sham and OXT neuron activated animals. After 3 weeks of CIH/H, MAP increased to hypertensive levels in sham animals (from a MAP of 102±3.3 mmHg on control days to 120±0.5 mmHg on day 21; n=7; $^+$p<0.01; one-way ANOVA with repeated measures; FIG. 12). Interestingly, animals receiving daily PVN OXT neuron activation experienced no significant changes in MAP throughout the 21 days of OHM exposure (from a MAP of 104±2.6 mmHg on control days to 103±3.0 mmHg on day 21; n=8; p>0.05; one-way ANOVA with repeated measures; FIG. 12). Animals in the sham group experienced significant increases in MAP from day 12 through day 21, whereas the increase in MAP was prevented in the DREADDs-expressing animals (Day 12: MAP in sham group of 117±4.1 mmHg, MAP in DREADDs-expressing group of 105±2.6 mmHg; Day 15: MAP in sham group of 118±2.6 mmHg, MAP in DREADDs-expressing group of 105±3.1 mmHg; Day 18: MAP in sham group of 122±1.1 mmHg, MAP in DREADDs-expressing group of 104±2.9 mmHg; Day 21: MAP in sham group of 120±0.5 mmHg, MAP in DREADDs-expressing group of 103±3.0 mmHg; n=7 sham animals and 8 DREADDs-expressing animals; *p<0.01; two-way ANOVA with repeated measures; FIG. 12). These data indicate that chronic activation of PVN OXT neurons prevents the development of hypertension that occurs in sham animals with CIH/H exposure.

Example 14

Administration of Oxytocin to Human Patients Improves Sleep Quality and Shows Cardio-Protective Effect Patients recently diagnosed with OSA were recruited to test the effect of oxytocin administration on heart rate, apnea-hypopnea index, oxygen saturation, apnea duration, arousal index etc. The study is approved by the FDA (IND #120989). Patients were administered 40 IU of oxytocin intranasally about one hour prior to sleeping.

Figure 13:
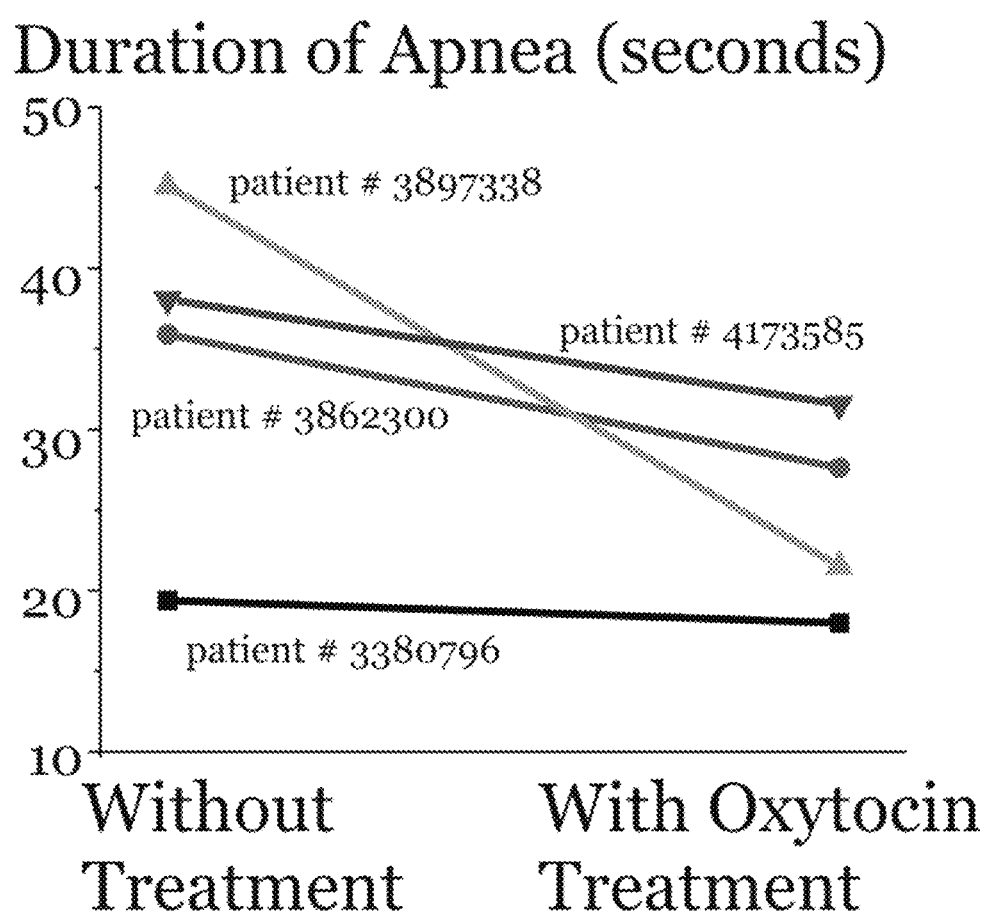
FIG. 13 shows that the nasal administration of oxytocin to OSA patients reduces the duration of apnea experienced by the patients.
Figure 14:
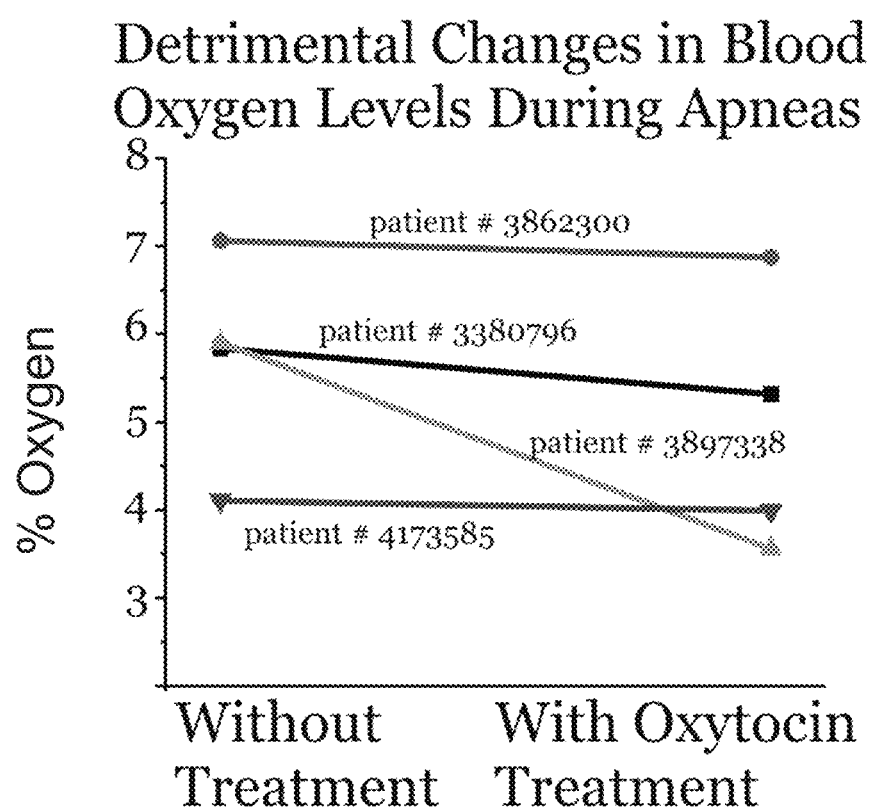
FIG. 14 shows adverse oxygen desaturations, in percent oxygen, that occur with and without the administration of oxytocin to OSA patients.
Figure 15:
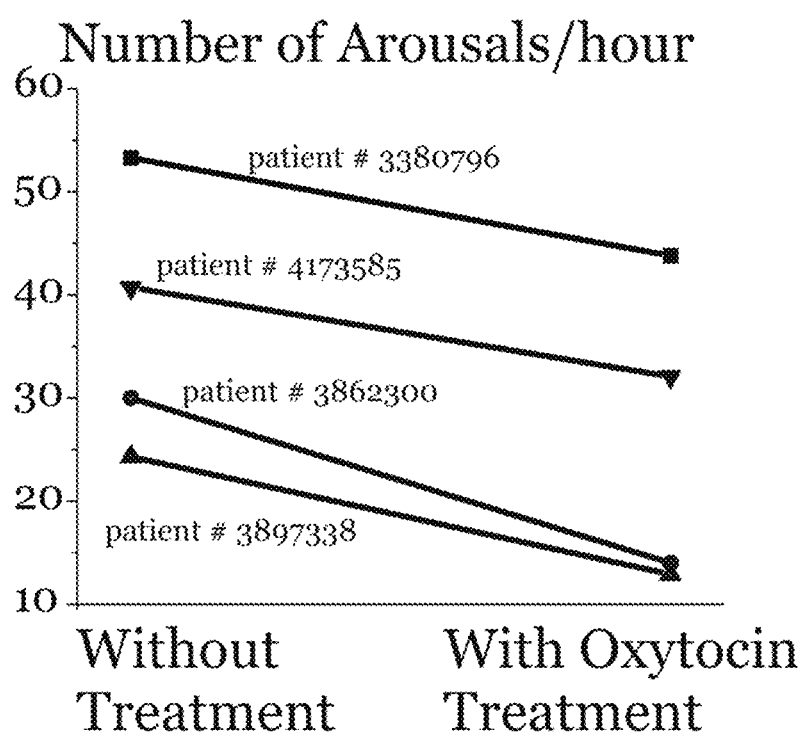
FIG. 15 shows that the nasal administration of oxytocin to OSA patients reduces the number of arousals per hour experienced by the patients.
Figure 16:
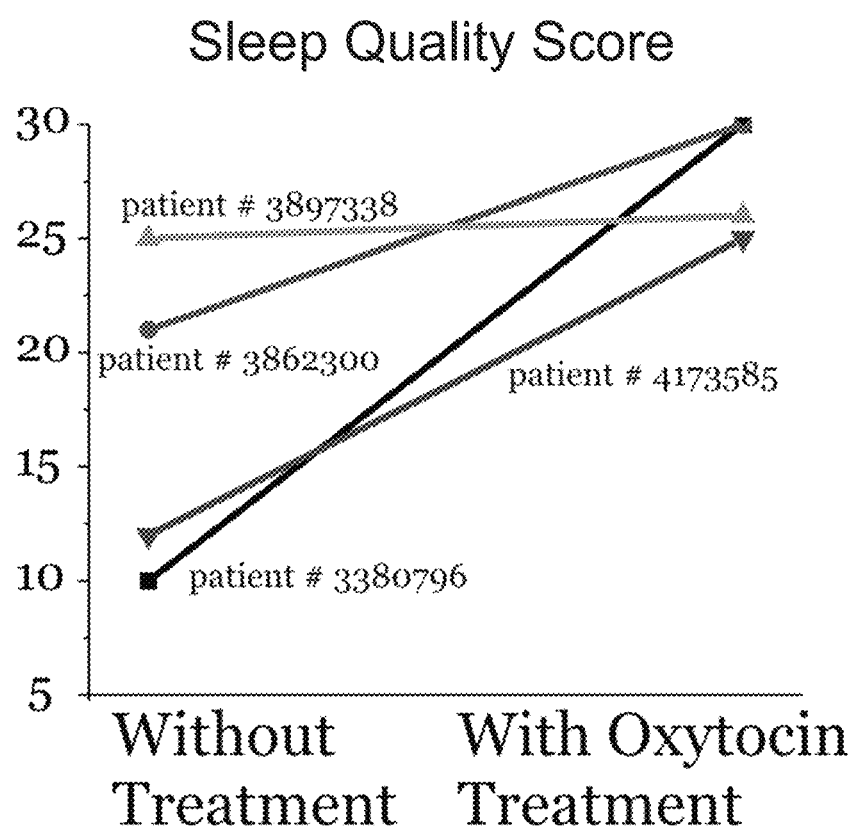
FIG. 16 shows the nasal administration of oxytocin to OSA patients improves their sleep quality or sleep satisfaction.

The following eight outcomes were compared in the same patients prior to and after administration with oxytocin:
  basal heart rate before sleep (primary outcome)
  mean changes in heart rate with apneic and hypopneic events (primary outcome)
  apnea-hypopnea index (secondary outcome)
  percentage of time spent by the patient with oxygen saturations: >90%, >80% but <90%, and <80% (secondary outcome)
  duration of apneas
  oxygen desaturation during apneas (expressed as adverse desaturations in percent oxygen)
  numbers of arousals (expressed per hour)
  sleep quality The following information was recorded for each patient before and after the use of intranasal oxytocin:
1. Demographics—Age, gender, ethnicity, weight, BMI.
2. Physiological data:
  a. Basal heart rate before sleep
  b. Apnea-hypopnea index
  c. Mean changes in heart rate with apneic and hypopneic events
  d. Percentage of time spent by the patient with oxygen saturations: >90%, >80% but <90%, and <80%.
  e. Duration of apneas
  f. Oxygen desaturation during apneas (expressed as adverse desaturations in percent oxygen)
  g. Numbers of arousals (expressed per hour)
  h. Sleep quality
3. Standard of care sleep study data using PSG: Polysomnography (PSG) monitors many body functions during sleep, including brain (EEG), eye movements (EOG), muscle activity or skeletal muscle activation (EMG), heart rhythm (ECG), respiratory airflow, thoracic and abdominal respiratory effort, body position, limb movement, and oxygen saturation using pulse oximetry. Recording and scoring was done according to the standards set by the American Academy of Sleep Medicine.
4. Sleep quality score: Patients were asked to rank their responses using the scale of 1-5 for a set of empirical factors:
  1—Strongly disagree
  2—Slightly disagree
  3—Neither agree nor disagree
  4—Slightly agree
  5—Strongly agree
Empirical Factors:
  I feel more refreshed than usual this morning
  My quality of sleep last night was better than usual
  I slept deeper than usual last night
  I woke up fewer times than usual last night
  I slept longer than usual last night
  I feel better overall than usual this morning The study shows that nasal administration of oxytocin reduces the duration of apnea (FIG. 13), reduces oxygen desaturation (FIG. 14), decreases the number of arousals/hour (FIG. 15), and improves sleep satisfaction (FIG. 16).

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

1. Armour J A (2008). Potential clinical relevance of the 'little brain' on the mammalian heart. *Exp Physiol* 93, 165-176.
2. Batten T F (1995). Immunolocalization of putative neurotransmitters innervating autonomic regulating neurons (correction of neurones) of cat ventral medulla. *Brain Res Bull* 37, 487-506.
3. Boychuk C R, Woerman A L & Mendelowitz D (2012). Modulation of bulbospinal rostral ventral lateral medulla neurons by hypoxia/hypercapnia but not medullary respiratory activity. *Hypertension* 60, 1491-1497.
4. Braga V A, Burmeister M A, Sharma R V & Davisson R L (2008), Cardiovascular responses to peripheral chemoreflex activation and comparison of different methods to evaluate baroreflex gain in conscious mice using telemetry. *Am J Physiol Regal Integr Comp Physiol* 295, R1168-1174.
5. Campen M J, Shimoda L A & O'Donnell C P (2005). Acute and chronic cardiovascular effects of intermittent hypoxia in C57BL/6J mice. *J. Appl Physiol* 99, 2028-2035.
6. Carlson J T, Hedner J A, Sellgren J, Elam M & Wallin B G (1996). Depressed baroreflex sensitivity in patients with obstructive sleep apnea. *Am J Respir Crit Care Med* 154, 1490-1496.
7. Chitravanshi V C, Agarwal S K & Calaresu F R (1991). Microinjection of glycine into the nucleus ambiguos elicits tachycardia in spinal rats. *Brain Res* 566, 290-294.
8. Dergacheva O, Boychuk C R & Mendelowitz D (2013). Developmental changes in GABAergic neurotransmission to presympathetic and cardiac parasympathetic neurons in the brainstem. *J Neurophysiol* 110, 672-679.
9. Fletcher E C, Bao G & Li R (1999), Renin activity and blood pressure in response to chronic episodic hypoxia. *Hypertension* 34, 309-314.
10. Fletcher E C, Lesske J. Behm R, Miller C C, 3rd, Stauss H & Unger T (1992). Carotid chemoreceptors, systemic blood pressure, and chronic episodic hypoxia mimicking sleep apnea. *J Appl Physiol* 72, 1978-1984.
11. Fletcher E C, Orolinova N & Bader M (2002). Blood pressure response to chronic episodic hypoxia: the renin-angiotensin system. *J Appl Physiol* 92, 627-633.
12. Frank J G, Jameson H S, Gorini C & Mendelowitz D (2009). Mapping and identification of GABAergic neurons in transgenic mice projecting to cardiac vagal neurons in the nucleus ambiguus using photo-uncaging. *j Neurophysiol* 101, 1755-1760.
13. Freet C S, Stoner J F & Tang X (2013). Baroreflex and chemoreflex controls of sympathetic activity following intermittent hypoxia. *Auton Neurosci* 174, 8-14.
14. Griffioen K J, Kamendi H W, Gorini C J, Bouairi E & Mendelowitz D (2007). Reactive oxygen species mediate central cardiorespiratory network responses to acute intermittent hypoxia. *J Neurophysiol* 97, 2059-2066.
15. Gu H, Lin M, Liu J, Gozal D, Scrogin K E, Wurster R, Chapleau M W, Ma X & Cheng Z J (2007). Selective impairment of central mediation of baroreflex in anesthetized young adult Fischer 344 rats after chronic intermittent hypoxia. *Am J Physiol Heart Circ Physiol* 293, H2809-2818.
16. Kc P, Balan K V, Tjoe S S, Martin R J, Lamanna J C, Haxhiu M A & Dick T E (2010). Increased vasopressin transmission from the paraventricular nucleus to the rostral medulla augments cardiorespiratory outflow in chronic intermittent hypoxia-conditioned rats. *J Physiol* 588, 725-740.
17. Kline D D (2010). Chronic intermittent hypoxia affects integration of sensory input by neurons in the nucleus tractus solitarii. *Respir Physiol Neurobiol* 174, 29-36.
18. Kline D D, Ramirez-Navarro A & Kunze D L (2007). Adaptive depression in synaptic transmission in the nucleus of the solitary tract after in vivo chronic intermittent hypoxia: evidence for homeostatic plasticity. *J Neurosci* 27, 4663-4673.
19. Konecny T, Kara T & Somers V K (2014). Obstructive sleep apnea and hypertension: an update. *Hypertension* 63, 203-209.
20. Lai O, Yang C C, Hsu Y Y, Lin Y N & Kuo T B (2006). Enhanced sympathetic outflow and decreased baroreflex sensitivity are associated with intermittent hypoxia-induced systemic hypertension in conscious rats. *J Appl Physiol* 100, 1974-1982.
21. Lin M, Ai J. Li L, Huang C, Chapleau M W, Liu R, Gozal D, Wead W B, Wurster R D & Cheng Z (2008). Structural remodeling of nucleus ambiguus projections to cardiac ganglia following chronic intermittent hypoxia in C57BL/6J mice. *J Comp Neurol* 509, 103-117.
22. Lin M, Liu R, Gozal D, Wead W B, Chapleau M W, Wurster R & Cheng Z J (2007). Chronic intermittent hypoxia impairs baroreflex control of heart rate but enhances heart rate responses to vagal efferent stimulation in anesthetized mice. *Am J Physiol Heart Circ Physiol* 293, H997-1006.
23. Mendelowitz D (1996). Firing properties of identified parasympathetic cardiac neurons in nucleus ambiguus. *Am J Physiol* 271, H2609-2614.
24. Mendelowitz D (1999). Advances in Parasympathetic Control of Heart Rate and Cardiac Function. *News Physicol Sci* 14, 155-161.
25. Mendelowitz D & Kunze D L (1991). Identification and dissociation of cardiovascular neurons from the medulla for patch clamp analysis. *Neurosci Lett* 132, 217-221.
26. Neff R A, Mihalevich M & Mendelowitz D (1998). Stimulation of NTS activates NMDA and non-NMDA receptors in rat cardiac vagal neurons in the nucleus ambiguus. *Brain Res* 792, 277-282.
27. Neff R A, Simmens S J, Evans C & Mendelowitz D (2004). Prenatal nicotine exposure alters central cardiorespiratory responses to hypoxia in rats: implications for sudden infant death syndrome, *J Neurosci* 24, 9261-9268,
28. Peng Y, Kline D D, Dick T E & Prabhakar N R (2001), Chronic intermittent hypoxia enhances carotid body chemoreceptor response to low oxygen. *Adv Exp Med Biol* 499, 33-38.
29. Peng Y J & Prabhakar N R (2004). Effect of two paradigms of chronic intermittent hypoxia on carotid body sensory activity. *J Appl Physiol* 96, 1236-1242; discussion 1196.
30. Sanchez-de-la-Torre M, Campos-Rodriguez F & Barbe F (2013). Obstructive sleep apnoea and cardiovascular disease. *Lancet Respir Med* 1, 61-72.
31. Schuen J N, Bamford O S & Carroll J L (1997). The cardiorespiratory response to anoxia: normal development and the effect of nicotine. *Respir Physiol* 109, 231-239.
32. Sharpe A L, Calderon A S, Andrade M A, Cunningham J T, Mifflin S W & Toney G M (2013). Chronic intermittent hypoxia increases sympathetic control of blood pressure: role of neuronal activity in the hypothalamic paraventricular nucleus. *Am J Physicol Heart Circ Physiol* 305, H1772-1780.
33. Soukhova-O'Hare G K, Cheng Z J, Roberts A M & Gozal D (2006). Postnatal intermittent hypoxia alters baroreflex function in adult rats. *Am J Physiol Heart Circ Physicol* 290, H1157-1164.
34. Taylor E W & Butler P J (1982). Nervous control of heart rate: activity in the cardiac vagus of the dogfish. *J Appl Physiol Respir Environ Exerc Physiol* 53, 1330-1335.
35. Trimer R, Mendes R G, Costa. F S, Sampaio L M, Delfino A, Jr., Arena R, Aletti F, Ferrario M & Borghi-Silva A (2013). Is there a chronic sleep stage-dependent 36. Wang J, Imaten M & Mendelowitz D (2001). Characteristics of spontaneous and evoked GABAergic synaptic currents in cardiac vagal neurons in rats. *Brain Res* 889, 78-83.
37. Wang J, Wang X, Imaten M, Venkatesan P, Evans C, Baxi S & Mendelowitz D (2003). Endogenous acetylcholine and nicotine activation enhances GABAergic and glycinergic inputs to cardiac vagal neurons. *J Neurophysiol* 89, 2473-2481.
38. Willis A, Mihalevich M, Neff R A & Mendelowitz D (1996). Three types of postsynaptic glutamatergic receptors are activated in DMNX neurons upon stimulation of NTS. *Am J Physicol* 271, R1614-1619.
39. Yan B, Li L, Harden S W, Gozal D, Lin Y, Wead W B, Wurster R D & Cheng Z J (2009). Chronic intermittent hypoxia impairs heart rate responses to AMPA and NMDA and induces loss of glutamate receptor neurons in nucleus ambiguous of F344 rats. *Am J Physiol Regal Integr Comp Physiol* 296, R299-308.
40. Yan B, Soukhova-O'Hare G K, Li L, Lin Y, Gozal D, Wead W B, Wurster R D & Cheng Z J (2008). Attenuation of heart rate control and neural degeneration in nucleus ambiguus following chronic intermittent hypoxia in young adult Fischer 344 rats. Neuroscience 153, 709-720.
41. Ye J H, Zhang Xiao C & Kong J Q (2006). Patch-clamp studies in the CNS illustrate a simple new method for obtaining viable neurons in rat brain slices: glycerol replacement of NaCl protects CNS neurons. *J Neurosci Methods* 158, 251-259.
42. Young T, Palta M, Dempsey J, Skatrud J, Weber S & Badr S (1993). The occurrence of sleep-disordered breathing among middle-aged adults. *N Engl J Med* 328, 1230-1235.
43. Zhao S, Ting J T, Atallah H E, Qiu L, Tan J, Gloss B, Augustine G J, Deisseroth K, Luo M, Graybiel A M & Feng G (2011). Cell type-specific channelrhodopsin-2 transgenic mice for optogenetic dissection of neural circuitry function. *Nat Methods* 8, 745-752.
44. Zoccal D B, Huidobro-Toro J P & Machado B H (2011). Chronic intermittent hypoxia augments sympatho-excitatory response to ATP but not to L-glutamate in the RVLM of rats. *Acton Neurosci* 165, 156-162.
45. Bradley T D, Floras J S. Obstructive sleep apnoea and its cardiovascular consequences. Lancet, 2009; 373:82-93.
46. Leung R S, Sleep-disordered breathing: autonomic mechanisms and arrhythmias. Prog Cardiovasc Dis. 2009; 51:324-38.
47. Loke Y K, Brown J W, Kwok C S, Niruban A, Myint P K. Association of obstructive sleep apnea with risk of serious cardiovascular events: a systematic review and meta-analysis. Circ Cardiovasc dual Outcomes. 2012; 5:720-8.
48. Bazzano L A, Khan Z, Reynolds K, He J. Effect of nocturnal nasal continuous positive airway pressure on blood pressure in obstructive sleep apnea. Hypertension. 2007; 50:417-23.
49. Carlson J T, Hedner J A, Sellgren J, Elam M, Wallin B G. Depressed baroreflex sensitivity in patients with obstructive sleep apnea. Am J Respir Crit Care Med. 1996; 154:1490-6.
50. Dyavanapalli J, Jameson H, Dergacheva O, Jain V, Alhusayyen M, Mendelowitz D. Chronic intermittent hypoxia-hypercapnia blunts heart rate responses and alters neurotransmission to cardiac vagal neurons. J Physiol. 2014; 592; 2799-811.
51. Lai C J, Yang C C, Hsu Y Y, Lin Y N, Kuo T B. Enhanced sympathetic outflow and decreased baroreflex sensitivity are associated with intermittent hypoxia-induced systemic hypertension in conscious rats. J Appl Physiol (1985). 2006; 100:1974-82.
52. Parish J M, Somers V K. Obstructive sleep apnea and cardiovascular disease. Mayo Clin Proc. 2004; 79:1036-46.
53. Pinol R A, Jameson H, Popratiloff A, Lee N H, Mendelowitz D. Visualization of oxytocin release that mediates paired pulse facilitation in hypothalamic pathways to brainstem autonomic neurons. PLoS One, 2014; 9:e112138,
54. Kc P, Dick T E, Modulation of cardiorespiratory function mediated by the paraventricular nucleus. Respir Physiol Neurobiol. 2010; 174:55-64.
55. McCall C, Singer I. The animal and human neuroendocrinology of social cognition, motivation and behavior, Nat Neurosci. 2012; 15:681-8.
56. Higa K T, Mori E, Viana F F, Morris M, Michelini L C. Baroreflex control of heart rate by oxytocin in the solitary-vagal complex. Am J Physiol Regul Integr Comp 2002; 282:R537-45.
57. Michelini L C, Marcelo M C, Amico J, Morris M. Oxytocinergic regulation of cardiovascular function: studies in oxytocin-deficient mice. Am J Physiol Heart Circ Physiol. 2003; 284:H2269-76.
58. Ring R H, Malberg J E, Potestio L, Ping J. Boikess S, Luo B, Schechter L E, Rizzo S, Rahman Z, Rosenzweig-Lipson S. Anxiolytic-like activity of oxytocin in male mice: behavioral and autonomic evidence, therapeutic implications. Psychopharmacology (Berl). 2006; 185: 218-25.
59. Dergacheva O, Dyavanapalli J, Pinol R A, Mendelowitz D. Chronic intermittent hypoxia and hypercapnia inhibit the hypothalamic paraventricular nucleus neurotransmission to parasympathetic cardiac neurons in the brain stem. Hypertension, 2014; 64:597-603.
60. Gamer M, Buchel C. Oxytocin specifically enhances valence-dependent parasympathetic responses. Psychoneuroendocrinology. 2012; 37:87-93.
61. Braga D C, Mori E, Higa K T, Morris M, Michelini L C. Central oxytocin modulates exercise-induced tachycardia. Am J Physiol Regal Integr Comp Physiol, 2000; 278: R1474-82.
62. McCann S M, Antunes-Rodrigues J, Jankowski M, Gutkowska J. Oxytocin, vasopressin and atrial natriuretic peptide control body fluid homeostasis by action on their receptors in brain, cardiovascular system and kidney. Prog Brain Res. 2002; 139:309-28.
63. Petersson M, Alster P, Lundeberg T, Uvnas-Moberg K. Oxytocin causes a long-term decrease of blood pressure in female and male rats. Physiol Behav. 1996; 60:1311-5.
64. Sawchenko P E, Swanson L W. Immunohistochemical identification of neurons in the paraventricular nucleus of the hypothalamus that project to the medulla or to the spinal cord in the rat. J Comp Neurol. 1982; 205:260-72.
65. Wsol A, Cudnoch-Je drzejewska A, Szczepanska-Sadowska E, Kowalewski S, Dobruch J. Central oxytocin modulation of acute stress-induced cardiovascular responses after myocardial infarction in the rat. Stress. 2009; 12:517-25.
66. Petersson M, Lundeberg T. Uvnas-Moberg K. Oxytocin decreases blood pressure in male but not in female spontaneously hypertensive rats. J Auton Nerv Syst. 1997; 66:15-8.

67. Hoist S, Uvnas-Moberg K, Petersson M. Postnatal oxytocin treatment and postnatal stroking of rats reduce blood pressure in adulthood. Auton Neurosci, 2002; 99:85-90.
68. Petersson M. Cardiovascular effects of oxytocin. Prog Brain Res. 2002; 139:281-8.
69, Kannan H, Niijima A, Yamashita H. Effects of stimulation of the hypothalamic paraventricular nucleus on blood pressure and renal sympathetic nerve activity. Brain Res Bull. 1988; 20:779-83,
70. Yamashita H, Kannan H, Kasai M, Osaka T. Decrease in blood pressure by stimulation of the rat hypothalamic paraventricular nucleus with L-glutamate or weak current. *J Auton Nerv Syst.* 1987; 19:229-34.
71. Lancel M, Kromer S, Neumann I D. Intracerebral oxytocin modulates sleep-wake behaviour in male rats. Regul Pept. 2003; 114(2-3):145-52.
72. U.S. Pre-grant Publication No. 2006/0252685.

What is claimed is:

1. A method for improving sleep quality in a patient suffering from obstructive sleep apnea, comprising: intranasally administering to the patient at least 40 International Units (IU) of oxytocin within an hour of the patient falling asleep,
   wherein the administration of oxytocin decreases the number of arousals per hour experienced by the patient during sleep.

2. The method of claim 1, wherein the administration of oxytocin decreases the number of arousals per hour by at least 10%.

3. The method of claim 1, wherein the patient is receiving continuous positive airway pressure (CPAP) therapy.

4. The method of claim 1, wherein the administration of oxytocin leads to improvement in empirical factors indicative of sleep quality in the patient.

5. The method of claim 1, wherein the administration of oxytocin leads to a decrease in the duration of apnea experienced by the patient during sleep.

6. The method of claim 5, wherein the administration of oxytocin decreases the duration of apnea by at least 10%.

7. The method of claim 1, wherein the administration of oxytocin decreases the oxygen desaturation experienced by the patient during sleep.

8. The method of claim 1, wherein the administration of oxytocin maintains or decreases the heart rate and/or blood pressure of the patient.

9. A method for treating obstructive sleep apnea in a patient receiving continuous positive airway pressure (CPAP) therapy, comprising: administering to the patient at least 40 International Units (IU) of oxytocin intranasally via the CPAP inhalation system within an hour of the patient falling asleep.

10. The method of claim 9, wherein the administration of oxytocin decreases the number of arousals per hour experienced by the patient during sleep by at least 10%.

11. The method of claim 9, wherein the administration of oxytocin leads to a decrease in the duration of apnea experienced by the patient during sleep.

12. The method of claim 11, wherein the administration of oxytocin decreases the duration of apnea by at least 10%.

13. The method of claim 9, wherein the administration of oxytocin decreases the oxygen desaturation experienced by the patient during sleep.

14. The method of claim 9, wherein the administration of oxytocin maintains or decreases the heart rate and/or blood pressure of the patient.

\* \* \* \* \*